(12) United States Patent
Hill et al.

(10) Patent No.: US 8,758,999 B2
(45) Date of Patent: Jun. 24, 2014

(54) METHODS AND COMPOSITIONS FOR THE DETECTION AND IDENTIFICATION OF ARCHAEA BASED ON THE TYPE II CHAPERONIN (THERMOSOME) GENE

(75) Inventors: Janet Elizabeth Hill, Saskatoon (CA); Bonnie Laura Chaban, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 13/637,487

(22) PCT Filed: Mar. 8, 2011

(86) PCT No.: PCT/CA2011/000264
§ 371 (c)(1),
(2), (4) Date: Sep. 26, 2012

(87) PCT Pub. No.: WO2011/116456
PCT Pub. Date: Sep. 29, 2011

(65) Prior Publication Data
US 2013/0189701 A1 Jul. 25, 2013

Related U.S. Application Data

(60) Provisional application No. 61/317,970, filed on Mar. 26, 2010.

(51) Int. Cl.
*C12Q 1/68* (2006.01)
(52) U.S. Cl.
USPC ......... 435/6.1; 435/6.11; 435/6.12; 435/91.2; 536/23.1; 536/23.7; 536/24.3; 536/24.33
(58) Field of Classification Search
USPC ............... 435/6.1, 6.11, 6.12, 91.2; 536/23.1, 536/23.7, 24.3, 24.33
See application file for complete search history.

(56) References Cited

U.S. PATENT DOCUMENTS

| | | | |
|---|---|---|---|
| 5,708,160 A | 1/1998 | Goh et al. | |
| 5,989,821 A | 11/1999 | Goh et al. | |
| 7,018,791 B1* | 3/2006 | Willison et al. | 435/4 |
| 7,129,329 B1* | 10/2006 | Alam et al. | 530/385 |
| 7,314,974 B2 | 1/2008 | Cao et al. | |
| 7,507,535 B2 | 3/2009 | Hill et al. | |
| 7,771,941 B2* | 8/2010 | Stroot et al. | 435/6.15 |

FOREIGN PATENT DOCUMENTS

WO 2010/005708 A2 1/2010

OTHER PUBLICATIONS

Archibald, J. et al. Recurrent paralogy in the evolution of archael chaperonins. Current Biology, Sep. 13, 1999, vol. 9, No. 18, pp. 1053-1056 and Supplementary material pp. S1-S6.

Janssen, P. et al. Structure of the archaeal community of the rumen. Applied and Environmental Microbiology, Jun. 2008, vol. 74, No. 12, pp. 3619-3625.
Hill, J. et al. CpnDB: A chaperonin sequence database. Genome Research, Aug. 2004, vol. 14, No. 8, pp. 1669-1675.
Baker, G. C. et al. 2003. Review and re-analysis of domain-specific 16S primers. Journal of Microbiological Methods 55:541-55, 2003.
Brousseau, R. et al. *Streptococcus suis* serotypes characterized by analysis of chaperonin 60 gene sequences. Applied and Environmental Microbiology, vol. 67, No. 10, p. 4828-4833, 2001.
Chaban, B. et al. Development of cpn60-based real-time quantitative PCR assays for the detection of 14 *Campylobacter* species and application to screening canine fecal samples. Applied and Environmental Microbiology, vol. 75, No. 10, p. 3055-3061, 2009.
Coetser, S. E. et al. Biofouling and biocorrosion in industrial water systems. Critical Reviews in Microbiology 31:213-232, 2005.
Delong, E. F. Archaea in coastal marine environments. Proc Natl Acad Sci USA, vol. 89, pp. 5685-5689, 1992.
Desai, A. R. et al. Characterization and quantification of feline fecal microbiota using cpn60 sequence-based methods and investigation of animal-to-animal variation in microbial population structure. Veterinary Microbiology 137:120-128, 2009.
Dumonceaux, T. J. et al. Enumeration of specific bacterial populations in complex intestinal communities using quantitative PCR based on the chaperonin-60 target. Journal of Microbiological Methods 64:46-62, 2006.
Dumonceaux, T. J. et al. Molecular characterization of microbial communities in Canadian pulp and paper activated sludge and quantification of a novel *Thiothrix eikelboomii*-like bulking filament. Canadian Journal of Microbiology 52:494-500, 2006.
Dumonceaux, T. J. et al. Characterization of intestinal microbiota and response to dietary virginiamycin supplementation in the broiler chicken. Applied and Environmental Microbiology, vol. 72, No. 4, pp. 2815-2823, 2006.
Dumonceaux, T. J. et al. Multiplex detection of bacteria associated with normal microbiota and with bacterial vaginosis in vaginal swabs using oligonucleotide-coupled fluorescent microspheres. Journal of Clinical Microbiology, vol. 47, No. 12, pp. 4067-4077, 2009.
Goh, S. H. et al. Identification of *Enterococcus* species and phenotypically similar *Lactococcus* and *Vagococcus* species by reverse checkerboard hybridization to chaperonin 60 gene sequences. Journal of Clinical Microbiology, vol. 38, No. 11, pp. 3953-3959, 2000.

(Continued)

*Primary Examiner* — Ardin Marschel
(74) *Attorney, Agent, or Firm* — Bereskin & Parr LLP; Camela DeLuca

(57) ABSTRACT

The present invention relates to primers for the universal amplification and detection of Archaea, which primers are designed based on a multiple sequence alignment of Archaea Type II chaperonin (thermo-some) genes. For detection of Archaea having templates with a GC content of below 60%, primers are designed so that inosine residues are found at degenerate positions. For amplification of higher GC content templates, degenerate positions are replaced with specific nucleotide bases found in the high GC organism. The primers are useful for detecting, identifying and quantifying Archaea in a sample and for determining a phylogenetic relationship of a test Archaea organism.

23 Claims, 12 Drawing Sheets

(56) References Cited

OTHER PUBLICATIONS

Haigh, J. C. et al. A novel clinical syndrome and detection of *Anaplasma ovis* in Mongolian reindeer (*Rangifer tarandus*). Journal of Wildlife Diseases 449(3), pp. 569-577, 2008.

Hill, J. E. et al. Extensive profiling of a complex microbial community by high-throughput sequencing. Applied and Environmental Microbiology, vol. 68, No. 6, pp. 3055-3066, 2002.

Hill, J. E. et al. Comparison of ileum microflora of pigs fed corn-, wheat-, or barley-based diets by chaperonin-60 sequencing and quantitative PCR. Applied and Environmental Microbiology, vol. 71, No. 2, pp. 867-875, 2005.

Hill, J. E., et al. Improved template representation in cpn60 PCR product libraries generated from complex templates by application of a specific mixture of PCR primers. Environmental Microbiology, vol. 8, No. 4, pp. 741-746, 2006.

Hill, J. E. et al. Characterization of vaginal microflora of healthy, nonpregnant women by chaperonin-60 sequence-based methods. American Journal of Obstetrics and Gynecology 193:682-92, 2005.

Large, A. T., et al. Archaeal chaperonins. Frontiers in Bioscience 14:1304-24, 2009.

Lazarovits, G. et al. Fish emulsion and liquid swine manure: model systems for development of organic amendments as fertilizers with disease suppressive properties, p. 49-68. In W. Bettiol and M. A. B. Morandi (ed.), Biocontrole de Doenças de Plantas : Uso e Perspectivas. Embrapa, Sao Paolo, 2009.

Leahy, S. C. et al. The genome sequence of the rumen methanogen *Methanobrevibacter ruminantium* reveals new possibilities for controlling ruminant methane emissions. PLoS One, vol. 5, Issue 1, e8926, 2010.

Masson, L. et al. Identification of pathogenic *Helicobacter* species by chaperonin-60 differentiation on plastic DNA arrays. Genomics 87:104-12, 2006.

Mihajlovski, A. et al. A putative new order of methanogenic Archaea inhabiting the human gut, as revealed by molecular analyses of the mcrA gene. Research in Microbiology 159:516-21, 2008.

Schellenberg, J. et al. Pyrosequencing of the chaperonin-60 universal target for phylogenetic analysis of microbial communities. Applied and Environmental Microbiology, vol. 75, No. 9, pp. 2889-2898, 2009.

Thompson, J. D. et al. Multiple sequence alignment using ClustalW and ClustalX. Current Protocols in Bioinformatics, Chapter 2:Unit 2, 3; 2003.

Vermette, C. J. et al. Resolution of phenotypically distinct strains of *Enterococcus* spp. in a complex microbial community using cpn60 universal target sequencing. Microbial Ecology 59:14-24, 2010 [Epub ahead of print]: doi:10.1007/s00248-009-9601-1.

Delong, Edward F. Microbial Community Genomics in the Ocean. Nature Reviews, Microbiology. vol. 3, Jun. 2005, p. 459-469.

Chaban Bonnie et al. Design and Evaluation of Universal Group II Chaperonin PCR Primers for Archaeal Detection. Poster and Abstract presented at the 13th International Symposium on Microbial Ecology Conference Aug. 22-27, 2010.

Chaban Bonnie et al. A 'universal' type II chaperonin PCR detection system for the investigation of Archaea in complex microbial communities. The ISME Journal, vol. 6, 430-439, Feb. 2012 (e-published Jul. 21, 2011).

\* cited by examiner

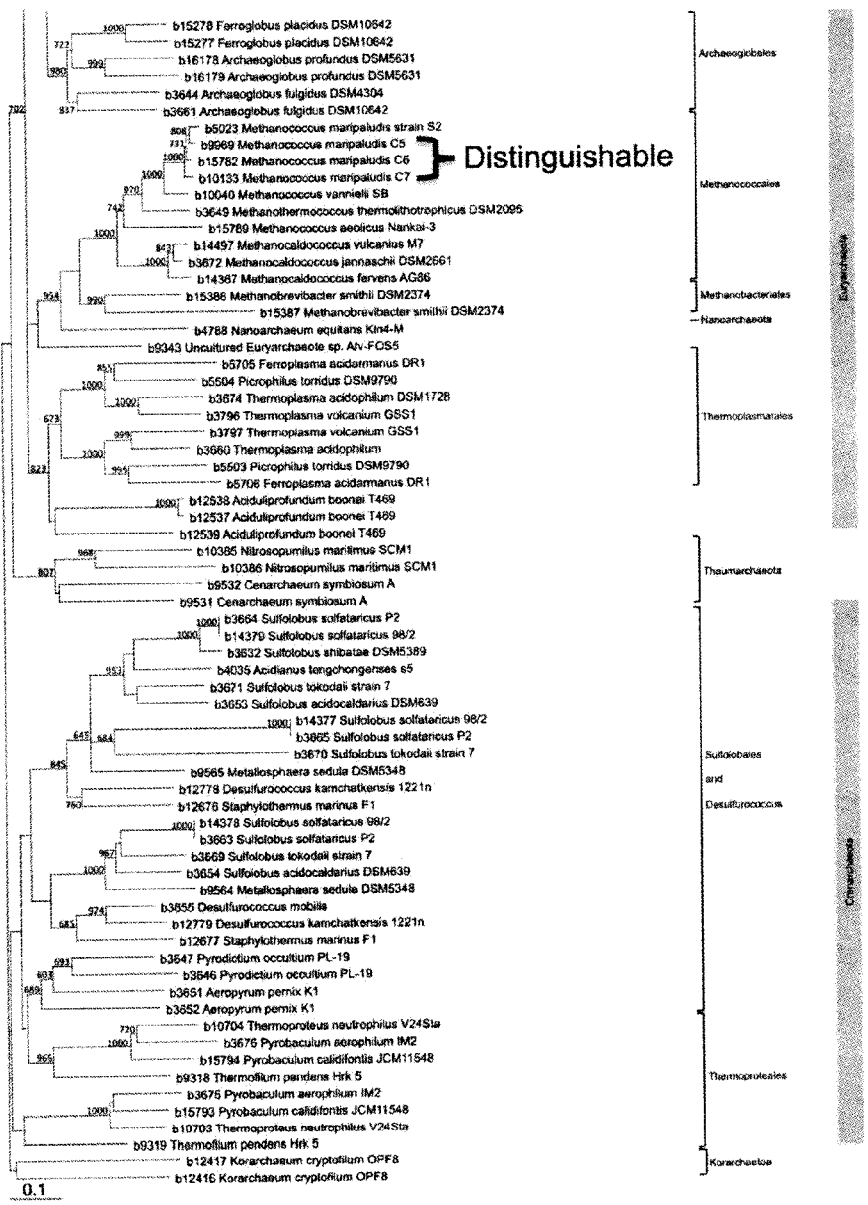
FIGURE 3 – CONTINUED

```
JH0175 (SEQ ID NO:3)  1 GGICCIMRRGGIITIGAYAARATG  24  Identity: 14/24 (58.3%)
                        ||.||....||..|.||.||.|||
JH0268 (SEQ ID NO:5)  1 GGCCCGAAGGGCATGGACAAGATG  24

JH0178 (SEQ ID NO:4)  1 GCIAIITCRTCIATICCYTTYTG   23  Identity: 15/23 (65.2%)
                        ||.|..||.||.||.||.||.||
JH0269 (SEQ ID NO:6)  1 GCCATGTCGTCGATGCCCTTCTG   23
```

Neighbour-joined trees were constructed from ClustalW aligned DNA sequences as the consensus of 100 replicates. Group II chaperonin subunits alpha, beta and gamma (when present) are indicated.

SEQUENCE LISTING

```
<160> NUMBER OF SEQ ID NOS: 6

<210> SEQ ID NO 1
<211> LENGTH: 24
<212> TYPE: DNA
<213> ORGANISM: Unknown
<220> FEATURE:
<223> OTHER INFORMATION: Archaea sp.
<220> FEATURE:
<221> NAME/KEY: misc_feature
<222> LOCATION: (3)..(3)
<223> OTHER INFORMATION: N  is I or C
<220> FEATURE:
<221> NAME/KEY: misc_feature
<222> LOCATION: (6)..(6)
<223> OTHER INFORMATION: N  is I or G
<220> FEATURE:
<221> NAME/KEY: misc_feature
<222> LOCATION: (7)..(7)
<223> OTHER INFORMATION: N  is A or C
<220> FEATURE:
<221> NAME/KEY: misc_feature
<222> LOCATION: (8)..(8)
<223> OTHER INFORMATION: N  is  A or G
<220> FEATURE:
<221> NAME/KEY: misc_feature
<222> LOCATION: (9)..(9)
<223> OTHER INFORMATION: N  is  A or G
<220> FEATURE:
<221> NAME/KEY: misc_feature
<222> LOCATION: (12)..(12)
<223> OTHER INFORMATION: N  is  I or C
<220> FEATURE:
<221> NAME/KEY: misc_feature
<222> LOCATION: (13)..(13)
<223> OTHER INFORMATION: N  is  I or A
<220> FEATURE:
<221> NAME/KEY: misc_feature
<222> LOCATION: (15)..(15)
<223> OTHER INFORMATION: N  is  I or G
```

```
<220> FEATURE:
<221> NAME/KEY: misc_feature
<222> LOCATION: (18)..(18)
<223> OTHER INFORMATION: N  is C or T
<220> FEATURE:
<221> NAME/KEY: misc_feature
<222> LOCATION: (21)..(21)
<223> OTHER INFORMATION: N  is A or G

<400> SEQUENCE: 1
ggnccnnnng gnntnganaa natg                                              24

<210> SEQ ID NO 2
<211> LENGTH: 23
<212> TYPE: DNA
<213> ORGANISM: Unknown
<220> FEATURE:
<223> OTHER INFORMATION: Archaea sp.
<220> FEATURE:
<221> NAME/KEY: misc_feature
<222> LOCATION: (3)..(3)
<223> OTHER INFORMATION: N is I or C
<220> FEATURE:
<221> NAME/KEY: misc_feature
<222> LOCATION: (5)..(5)
<223> OTHER INFORMATION: N is I or T
<220> FEATURE:
<221> NAME/KEY: misc_feature
<222> LOCATION: (6)..(6)
<223> OTHER INFORMATION: N is I or G
<220> FEATURE:
<221> NAME/KEY: misc_feature
<222> LOCATION: (9)..(9)
<223> OTHER INFORMATION: N is A or G
<220> FEATURE:
<221> NAME/KEY: misc_feature
<222> LOCATION: (12)..(12)
<223> OTHER INFORMATION: N is I or G
<220> FEATURE:
<221> NAME/KEY: misc_feature
<222> LOCATION: (15)..(15)
<223> OTHER INFORMATION: N is I or G
<220> FEATURE:
<221> NAME/KEY: misc_feature
<222> LOCATION: (18)..(18)
<223> OTHER INFORMATION: N is C or T
<220> FEATURE:
<221> NAME/KEY: misc_feature
<222> LOCATION: (21)..(21)
<223> OTHER INFORMATION: N is C or T

<400> SEQUENCE: 2
gcnanntcnt cnatnccntt ntg                                               23

<210> SEQ ID NO 3
<211> LENGTH: 24
<212> TYPE: DNA
<213> ORGANISM: Unknown
<220> FEATURE:
<223> OTHER INFORMATION: Archaea sp.
<220> FEATURE:
<221> NAME/KEY: misc_feature
<222> LOCATION: (3)..(3)
<223> OTHER INFORMATION: N is I, a, c, g or t
<220> FEATURE:
<221> NAME/KEY: misc_feature
<222> LOCATION: (6)..(6)
<223> OTHER INFORMATION: N is I, a, c, g or t
<220> FEATURE:
<221> NAME/KEY: misc_feature
<222> LOCATION: (12)..(12)
<223> OTHER INFORMATION: N is I, a, c, g or t
<220> FEATURE:
<221> NAME/KEY: misc_feature
<222> LOCATION: (13)..(13)
<223> OTHER INFORMATION: N is I, a, c, g, or t
```

```
<220> FEATURE:
<221> NAME/KEY: misc_feature
<222> LOCATION: (15)..(15)
<223> OTHER INFORMATION: N is I, a, c, g, or t

<400> SEQUENCE: 3
ggnccnmrrg gnntngayaa ratg                                              24

<210> SEQ ID NO 4
<211> LENGTH: 23
<212> TYPE: DNA
<213> ORGANISM: Unknown
<220> FEATURE:
<223> OTHER INFORMATION: Archaea sp.
<220> FEATURE:
<221> NAME/KEY: misc_feature
<222> LOCATION: (3)..(3)
<223> OTHER INFORMATION: N is I, a, c, g or t
<220> FEATURE:
<221> NAME/KEY: misc_feature
<222> LOCATION: (5)..(5)
<223> OTHER INFORMATION: N is I, a, c, g or t
<220> FEATURE:
<221> NAME/KEY: misc_feature
<222> LOCATION: (6)..(6)
<223> OTHER INFORMATION: N is I, a, c, g or t
<220> FEATURE:
<221> NAME/KEY: misc_feature
<222> LOCATION: (12)..(12)
<223> OTHER INFORMATION: N is I, a, c, g or t
<220> FEATURE:
<221> NAME/KEY: misc_feature
<222> LOCATION: (15)..(15)
<223> OTHER INFORMATION: N is I, a, c, g or t

<400> SEQUENCE: 4
gcnanntcrt cnatnccytt ytg                                               23

<210> SEQ ID NO 5
<211> LENGTH: 24
<212> TYPE: DNA
<213> ORGANISM: Unknown
<220> FEATURE:
<223> OTHER INFORMATION: Archaea sp.

<400> SEQUENCE: 5
ggcccgaagg gcatggacaa gatg                                              24

<210> SEQ ID NO 6
<211> LENGTH: 23
<212> TYPE: DNA
<213> ORGANISM: Unknown
<220> FEATURE:
<223> OTHER INFORMATION: Archaea sp.

<400> SEQUENCE: 6
gccatgtcgt cgatgcccttt ctg                                              23
```

US 8,758,999 B2

METHODS AND COMPOSITIONS FOR THE DETECTION AND IDENTIFICATION OF ARCHAEA BASED ON THE TYPE II CHAPERONIN (THERMOSOME) GENE

CROSS-REFERENCE TO RELATED APPLICATIONS

This application is a national phase entry of PCT/CA2011/000264, filed Mar. 8, 2011, which claims priority from U.S. Provisional patent application Ser. No. 61/317,970 filed Mar. 26, 2010; each of these applications being incorporated herein in their entirety by reference.

INCORPORATION OF SEQUENCE LISTING

A computer readable form of the Sequence Listing "SequenceListing.txt" (3851 bytes), created Mar. 8, 2011, is herein incorporated by reference.

FIELD OF THE DISCLOSURE

The disclosure relates to universal primers and methods for the amplification, detection, identification and/or quantification of Archaea organisms.

BACKGROUND OF THE DISCLOSURE

The prokaryotic world is divided into the Bacteria and Archaea domains. Although these two groups are evolutionarily and biochemically distinct, both are found in almost every environment investigated. The roles bacteria play in the environment are extensive, covering a range of functions from nutrient cycling to disease progression. Although our understanding of archaeal roles has lagged behind bacterial research, archaea are well-recognized components of many systems, from rumen digestion and the production of greenhouse gases from livestock (23) to microbiologically influenced corrosion and biofouling of industrial water systems and gas pipelines (4).

Because of the genetic distinction between the prokaryotic domains, molecular targeting of microbial populations must be domain-specific. Within the bacterial realm, robust universal polymerase chain reaction (PCR) primer sets have been well-characterized and utilized to target the bacterial 16S rRNA gene and the group I chaperonin (cpn60) gene (1, 18). Both have provided a wealth of data towards understanding the bacterial members of complex communities, with the protein-coding chaperonin gene having advantages in terms of phylogenetic resolution. Universal primers for the amplification of the cpn60 "universal target" sequence are patented (11, 12, 17) and have been widely applied to the detection, identification, quantification and phylogenetic analysis of bacteria and eukaryotes in clinical and environmental samples (2, 3, 6-10, 13-16, 19, 20, 22, 24, 26, 28). Within the archaeal realm, universal PCR primers for the entire domain have remained limited to the archaeal 16S rRNA gene (1). With the continued increase in publicly available archaeal genome sequences, it is now possible to investigate and evaluate non-16S rRNA gene targets as potential universal archaeal markers with improved resolving power over the 16S rRNA gene.

SUMMARY OF THE DISCLOSURE

In an aspect, the disclosure includes an isolated nucleic acid molecule comprising:

a) a polynucleotide comprising at least 10 contiguous nucleotides of: $GGX_{1u}$ $CCX_{2u}$ $X_{3u}X_{4u}X_{5u}$ $GGX_{6u}$ $X_{7u}TX_{8u}$ $GAX_{9u}$ $AAX_{10u}$ ATG (SEQ ID NO:1) or $GCX_{1d}$ $AX_{2d}X_{3d}$ $TCX_{4d}$ $TCX_{5d}$ $ATX_{8d}$ $CCX_{7d}$ $TTX_{8d}$ TG (SEQ ID NO:2);

b) a polynucleotide having at least 80% sequence identity to: $GGX_{1u}$ $CCX_{2u}$ $X_{3u}X_{4u}X_{5u}$ $GGX_{8u}$ $X_{7u}TX_{8u}$ $GAX_{9u}$ $AAX_{10u}$ ATG (SEQ ID NO:1) or $GCX_{1d}$ $AX_{2d}X_{3d}$ $TCX_{4d}$ $TCX_{5d}$ $ATX_{8d}$ $CCX_{7d}$ $TTX_{8d}$ TG (SEQ ID NO:2); or c) a polynucleotide reverse complementary to a) or b), wherein $X_{1u}$ is I or C; $X_{2u}$ is I or G; $X_{3u}$ is A or C; $X_{4u}$ is A or G; $X_{5u}$ is A or G; $X_{6u}$ is I or C; $X_{7u}$ is I or A; $X_{8u}$ is I or G; $X_{9u}$ is C or T; $X_{10u}$ is A or G; $X_{1d}$ is I or C; $X_{2d}$ is I or T; $X_{3d}$ is I or G; $X_{4d}$ is A or G; $X_{5d}$ is I or G; $X_{6d}$ is I or G; $X_{7d}$ is C or T; and $X_{8d}$ is C or T; and wherein the polynucleotide corresponds to a portion of an archaea thermosome polynucleotide.

In an embodiment, the disclosure includes an isolated nucleic acid molecule comprising:

a) a polynucleotide comprising at least 10 contiguous nucleotides of: GGI CCI MRR GGI ITI GAY AAR ATG (SEQ ID NO:3), CCI AII TCR TCI ATI CCY TTY TG (SEQ ID NO:4), GGC CCG AAG GGC ATG GAC AAG ATG (SEQ ID NO:5) or GCC ATG TCG TCG ATG CCC TTC TG (SEQ ID NO:6);

b) a polynucleotide having at least 80% sequence identity to: GGI CCI MRR GGI ITI GAY AAR ATG (SEQ ID NO:3), GCI AII TCR TCI ATI CCY TTY TG (SEQ ID NO:4), GGC CCG AAG GGC ATG GAC AAG ATG (SEQ ID NO:5) or GCC ATG TCG TCG ATG CCC TTC TG (SEQ ID NO:6); or c) a polynucleotide reverse complementary to a) or b); wherein the polynucleotide corresponds to a portion of an archaea thermosome polynucleotide.

In an embodiment, the polynucleotide has at least 85%, 90%, 95%, 96%, 97%, 98%, 99% or 99.5% sequence identity to any one of SEQ ID NOs:1 to 6.

In an embodiment, the isolated nucleic acid molecule is a probe. In an embodiment, the isolated nucleic acid molecule is a polynucleotide primer.

In another aspect the disclosure includes a set of polynucleotide primers for amplification of a portion of an archaea thermosome polynucleotide, the primer set comprising:

a) one or more upstream primers comprising a polynucleotide comprising at least 10 contiguous nucleotides of: $GGX_{1u}$ $CCX_{2u}$ $X_{3u}X_{4u}X_{6u}$ $GGX_{6u}$ $X_{7u}TX_{8u}$ $GAX_{9u}$ $AAX_{10u}$ ATG (SEQ ID NO:1); and one or more downstream primers comprising a polynucleotide, the polynucleotide comprising at least 10 contiguous nucleotides of: $GCX_{1d}$ $AX_{2d}X_{3d}$ $TCX_{4d}$ $TCX_{5d}$ $ATX_{6d}$ $CCX_{7d}TTX_{8d}$ TG (SEQ ID NO:2); or b) one or more upstream primers comprising a polynucleotide comprising at least 10 contiguous nucleotides of a sequence reverse complementary to: $GGX_{1u}$ $CCX_{2u}$ $X_{3u}X_{4u}X_{5u}$ $GGX_{6u}$ $X_{7u}TX_{8u}$ $GAX_{9u}$ $AAX_{10u}$ ATG (SEQ ID NO:1); and one or more downstream primers comprising a polynucleotide comprising at least 10 contiguous nucleotides of a sequence reverse complementary to: $GCX_{1d}AX_{2d}X_{3d}$ $TCX_{4d}$ $TCX_{5d}$ $ATX_{6d}$ $CCX_{7d}$ $TTX_{8d}$ TG (SEQ ID NO:2).

In an embodiment, the primer set comprises:

a) one or more upstream primers comprising a polynucleotide comprising at least 10 contiguous nucleotides of: GGI CCI MRR GGI ITI GAY AAR ATG (SEQ ID NO:3) or GGC CCG AAG GGC ATG GAC AAG ATG (SEQ ID NO:5); and one or more downstream primers comprising a polynucleotide comprising at least 10 contiguous nucleotides of: GCI AII TCR TCI ATI CCY TTY TG (SEQ ID NO:4) or GCC ATG TCG TCG ATG CCC TTC TG (SEQ ID NO:6); or b) one or more upstream primers comprising a polynucleotide comprising at least 10 contiguous nucleotides of a sequence reverse complementary to: GGI CCI MRR GGI ITI GAY MR ATG (SEQ ID NO:3) or GGC CCG AAG GGC ATG GAC AAG ATG (SEQ ID NO:5); and one or more downstream primers comprising a polynucleotide comprising at least 10 contiguous nucleotides of a sequence reverse complementary to: GGI GCI AII TCR TCI ATI CCY TTY TG (SEQ ID NO:4) or GCC ATG TCG TCG ATG CCC TTC TG (SEQ ID NO:6).

In an embodiment, the primer set comprises: a first primer pair comprising a polynucleotide consisting of GGI CCI MRR GGI ITI GAY MR ATG (SEQ ID NO:3) and a polynucleotide consisting of GCI AII TCR TCI ATI CCY TTY TG (SEQ ID NO:4), and a second primer pair comprising a polynucleotide consisting of GGC CCG AAG GGC ATG GAC MG ATG (SEQ ID NO:5) and a polynucleotide consisting of GCC ATG TCG TCG ATG CCC TTC TG (SEQ ID NO:6), wherein the ratio of the first primer pair to the second primer pair is about 7:1, 3:1 or 1:1.

In an embodiment, the primer set comprises: a polynucleotide consisting of GGI CCI MRR GGI ITI GAY MR ATG (SEQ ID NO:3) and a polynucleotide consisting of GCI AII TCR TCI ATI CCY TTY TG (SEQ ID NO:4) and a second primer pair comprising a polynucleotide consisting of GGC CCG MG GGC ATG GAC MG ATG (SEQ ID NO:5) and a polynucleotide consisting of GCC ATG TCG TCG ATG CCC TTC TG (SEQ ID NO:6), and wherein the ratio of the first primer pair to the second primer pair is about 1:7, 1:3, 1:1, 3:1, 7:1, 15:1, 31:1, 63:1, 127:1 and 255:1 or any ratio between 1:7 and 255:1.

Another aspect of the disclosure includes a method of amplifying an archaea thermosome polynucleotide comprising:
  a) providing a sample comprising at least one archaea thermosome polynucleotide target;
  b) adding a primer set for amplification of the thermosome polynucleotide target(s) comprising a primer set described herein; and
  c) incubating the sample under conditions and with reagents for DNA amplification;
wherein each primer is annealed to the thermosome polynucleotide target at a position enabling amplification of the thermosome polynucleotide target and a DNA polymerase amplifies the thermosome polynucleotide target.

In an embodiment, wherein the archaea thermosome polynucleotide is RNA such as RNA, the method comprises reverse transcribing the RNA to provide thermosome cDNA polynucleotide target, for example using a RT-polymerase, prior to adding a primer set for amplification of the thermosome cDNA polynucleotide target.

Another aspect of the disclosure includes a method of detecting the presence or absence of an archaea organism in a sample comprising contacting the sample with a nucleic acid probe or primer which selectively hybridizes to an archaea thermosome polynucleotide target and determining whether the nucleic acid probe or primer binds to the thermosome polynucleotide target, wherein binding is indicative of the presence of the archaea organism in the sample.

In yet another aspect, the disclosure includes a method of detecting the presence or absence of an archaea organism in a sample comprising amplifying an archaea thermosome polynucleotide according to the methods described herein to provide an amplified archaea thermosome polynucleotide and detecting the amplified thermosome polynucleotide, wherein the detecting of the amplified thermosome polynucleotide is indicative of the presence of the archaea organism in the sample.

A further aspect of the disclosure includes a method for quantifying a concentration of one or more species of an archaea organism comprising quantitatively amplifying an archaea thermosome polynucleotide using the primer sets described herein, and comparing the amplified thermosome polynucleotide to a quantitative standard.

A further aspect of the disclosure includes a method for identifying a species of an archaea organism comprising:
  a) amplifying an archaea thermosome polynucleotide according to the methods described herein to provide an amplified archaea thermosome polynucleotide;
  b) determining the amplified thermosome polynucleotide sequence; and
  c) identifying the species of the archaea organism.

In another aspect, the disclosure includes a method of determining a phylogenetic relationship of a test archaea organism comprising:
  a) amplifying an archaea thermosome polynucleotide of the test archaea organism as described herein to provide an amplified archaea thermosome polynucleotide;
  b) determining the amplified thermosome polynucleotide sequence; and
  c) comparing the amplified thermosome polynucleotide sequence to one or more corresponding thermosome nucleotide sequences of one or more known archaea species;
wherein the phylogenetic relationship is determined by sequence similarity to the one or more known archaea species.

Another aspect of the disclosure includes a method for assessing a test substance for its effect on gastrointestinal archaea makeup in a subject comprising:
  a) obtaining a first sample comprising archaea organisms from the subject;
  b) administering the test substance;
  c) obtaining a second sample putatively comprising archaea organisms from the subject; and
  d) identifying the archaea organisms species according to the methods described herein and/or quantifying the concentration of each species of archaea organisms in the first and second samples according to the methods described herein;
wherein a difference in the archaea species and/or a difference in the concentration of one or more species is indicative that the test substance has effect on gastrointestinal archaea makeup in the subject.

A kit comprising:
  a. a polynucleotide comprising at least 10 contiguous nucleotides of: $GGX_{1u}$ $CCX_{2u}$ $X_{3u}X_{4u}X_{5u}$ $GGX_{6u}$ $X_{7u}TX_{8u}$ $GAX_{9u}$ $AAX_{10u}$ ATG (SEQ ID NO:1) or $GCX_{1d}$ $AX_{2d}X_{3d}$ $TCX_{4d}$ $TCX_{5d}$ $ATX_{6d}$ $CCX_{7d}$ $TTX_{8d}$ TG (SEQ ID NO:2);
  b. a polynucleotide having at least 80% sequence identity to: $GGX_{1u}$ $CCX_{2u}$ $X_{3u}X_{4u}X_{5u}$ $GGX_{6u}$ $X_{7u}TX_{8u}$ $GAX_{9u}$ $AAX_{10u}$ ATG (SEQ ID NO:1) and/or $GCX_{1d}$ $AX_{2d}X_{3d}$ $TCX_{4d}$ $TCX_{5d}$ $ATX_{6d}$ $CCX_{7d}$ $TTX_{8d}$ TG (SEQ ID NO:2); or
  c. a polynucleotide reverse complementary to a) or b), wherein $X_{1u}$ is I or C; $X_{2u}$ is I or G; $X_{3u}$ is A or C; $X_{4u}$ is A or G; $X_5$, is A or G; $X_{6u}$ is I or C; $X_{7u}$ is I or A; $X_{8u}$ is I or G; $X_{9u}$ is C or T; $X_{10u}$ is A or G;

$X_{1d}$ is I or C; $X_{2d}$ is I or T; $X_{3d}$ is I or G; $X_{4d}$ is A or G; $X_{gd}$ is I or G; $X_{6d}$ is I or G; $X_{7d}$ is C or T; and $X_{8d}$ is C or T; and wherein the polynucleotide corresponds to a portion of an archaea thermosome polynucleotide.

A kit for the detection of an archaea thermosome polynucleotide comprising:

a) a polynucleotide comprising at least 10 contiguous nucleotides of: GGI CCI MRR GGI ITI GAY AAR ATG (SEQ ID NO:3), GCI AII TCR TCI ATI CCY TTY TG (SEQ ID NO:4), GGC CCG AAG GGC ATG GAC AAG ATG (SEQ ID NO:5) or GCC ATG TCG TCG ATG CCC TTC TG (SEQ ID NO:6);

b) a polynucleotide having at least 80% sequence identity to: GGI CCI MRR GGI ITI GAY AAR ATG (SEQ ID NO:3), GCI AII TCR ICI ATI CCY TTY TG (SEQ ID NO:4), GGC CCG AAG GGC ATG GAC AAG ATG (SEQ ID NO:5) or GCC ATG TCG TCG ATG CCC TTC TG (SEQ ID NO:6); or c) a polynucleotide reverse complementary to a) and/or b) wherein the polynucleotide corresponds to a portion of an archaea thermosome polynucleotide.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

(B) PCR products from the SEQ ID NO:3/SEQ ID NO:4 primer set (A), the SEQ5/SEQ6 primer set (B) and a 7:1 ratio cocktail of SEQ3/SEQ4:SEQ5/SEQ6 primer mixture (C) using 1.0 ng/reaction of genomic DNA from archaeal isolates as templates. Lanes indicate (NTC) PCR no template control; (Neg) *Escherichia coli* DH5α; (1) *Methanococcus voltae*; (2) *Methanococcus vannielii*; (3) *Methanococcus maripaludis*; (4) *Methanotorris igneus*; (5) *Methanospirillum hungarei*; (6) *Sulfolobus solfataricus*; (7) *Sulfolobus* sp.; (8) *Thermoplasma acidophilum*; (9) *Thermococcus gorgonarius*; (10) *Thermococcus pacificus*; (11) *Thermococcus zilligii*; (12) *Halobacterium salinarum* (formerly *Halobacterium halobium*); (13) *Halobacterium salinarum* (formerly *Halobacterium cutirubrum*); (14) *Halobacterium salinarum* (formerly

*Halobacterium salinarium*); (15) *Haloferax volcanii* WR341; (16) *Haloferax volcanii* WR536.

Figure 10:
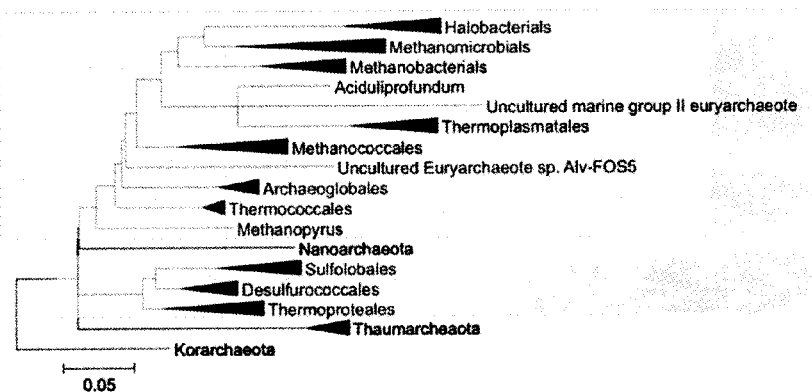
Figure 10:
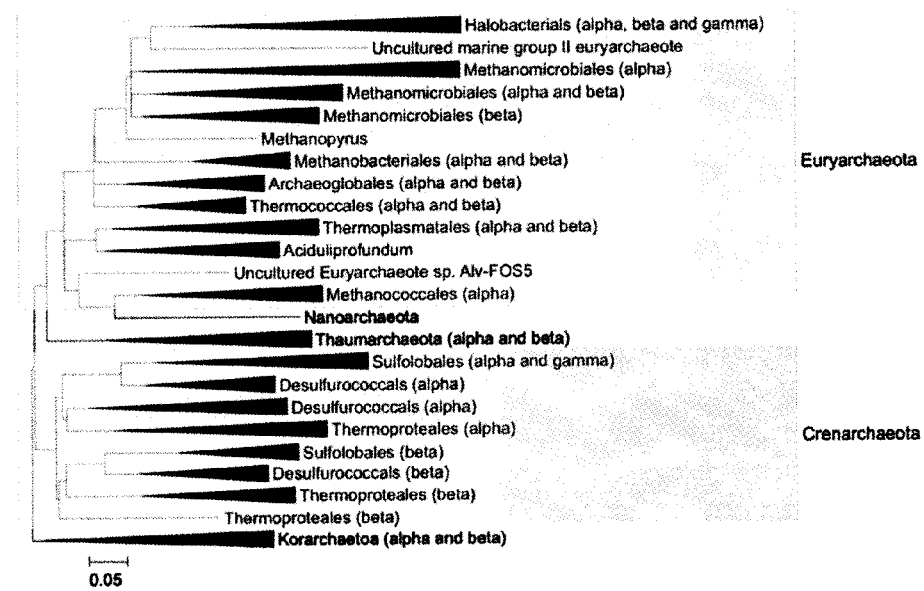

FIG. 10 Universal target (about 750 bp) group II chaperonin phylogeny

Figure 11:
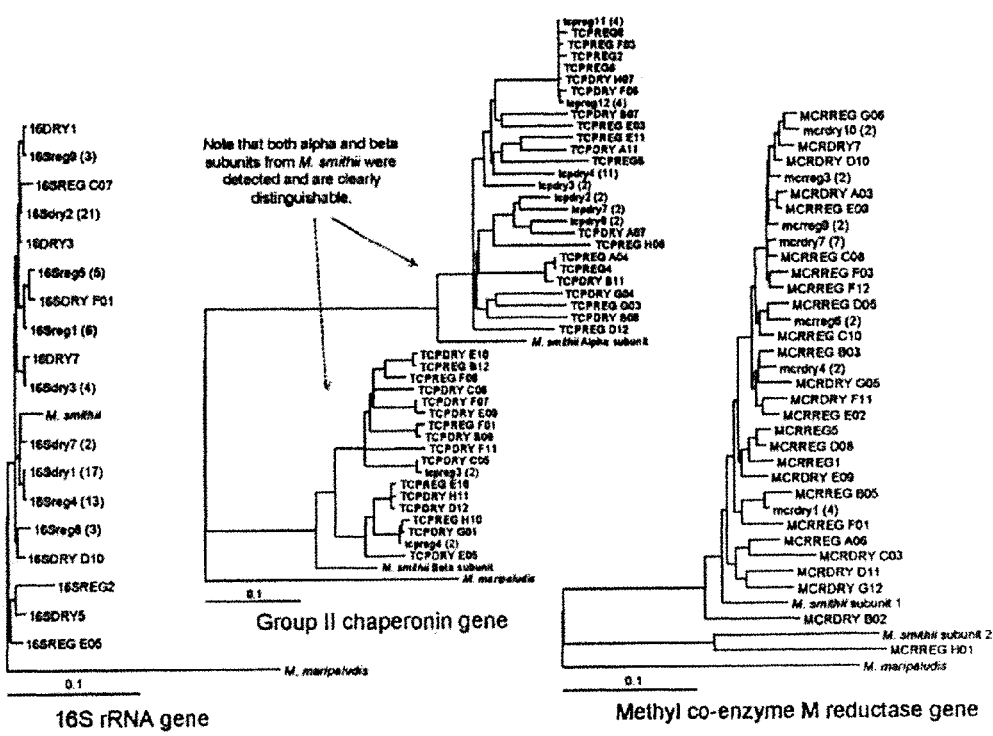

FIG. 11 Neighbour-joined phylogenetic trees of sequences identified as *Methanobrevibacter smithii*

DETAILED DESCRIPTION OF THE DISCLOSURE

Type II archaeal chaperonins (known as the thermosome, TF55, CCT or TCP-1), are essential genes involved in protein folding in the cell (21). Depending on the species, archaea contain from 1 to 3 distinct copies of the thermosome gene in their genome. Given the fact that this gene is ubiquitous in nature, thermosome DNA sequences were collected from publicly available datasets and evaluated for potential universal PCR primer sites. A set of primers, designated JH0175 (5'-GGI CCI MRR GGI ITI GAY MR ATG-3') (SEQ ID NO:3) and JH0178 (5'-GCI AII TCR TCI ATI CCY TTY TG-3') (SEQ ID NO:4), were designed, synthesized and tested against a panel of purified genomic DNA from a wide range of archaeal species. In addition, field samples of rumen contents from dairy cows were evaluated by PCR for archaeal DNA with both the thermosome primer set and as well as established 16S primer sets. The thermosome primer set performed as well as the established primer sets on purified DNA in the laboratory for isolates with GC contents below 60% (all archaeal groups except the halophiles) and outperformed the established primers on field samples.

To address amplification with higher G+C content templates, PCR primers targeting the highest G+C content organism, *Halobacterium salinarum* (66% G+C) were designed. Degenerate positions in JH0175 and JH0178 (I, M, R, and Y) were replaced with specific nucleotide bases found in the high G+C organism. These primers are designated JH0268 (5'-GGC CCG AAG GGC ATG GAC MG ATG-3') (SEQ ID NO:5) and JH0269 (5'-GCC ATG TCG TCG ATG CCC TTC TG-3') (SEQ ID NO:6) and anneal to the same sites targeted by JH0175 and JH0178 primers.

Accordingly, in an aspect the disclosure includes an isolated nucleic acid molecule comprising:
 a. a polynucleotide comprising at least 10 contiguous nucleotides of: $GGX_{1u}$ $CCX_{2u}$ $X_{3u}X_{4u}X_{5u}$ $GGX_{6u}$ $X_{7u}TX_{8u}$ $GAX_{9u}$ $AAX_{10u}$ ATG (SEQ ID NO:1) or $GCX_{1d}$ $AX_{2d}X_{3d}$ $TCX_{4d}$ $TCX_{5d}$ $ATX_{6d}$ $CCX_{7d}$ $TTX_{8d}$ TG (SEQ ID NO:2);
 b. a polynucleotide having at least 80% sequence identity to: $GGX_{1u}$ $CCX_{2u}$ $X_{3u}X_{4u}X_{5u}$ $GGX_{6u}$ $X_{7u}TX_{9u}$ $GAX_{9u}$ $AAX_{10u}$ ATG (SEQ ID NO:1) or $GCX_{1d}$ $AX_{2d}X_{3d}$ $TCX_{4d}$ $TCX_{5d}$ $ATX_{6d}$ $CCX_{7d}$ $TTX_{8d}$ TG (SEQ ID NO:2); or
 c. a polynucleotide reverse complementary to a) or b), wherein
 $X_{1u}$ is I or C; $X_{2u}$ is I or G; $X_{3u}$ is A or C; $X_{4u}$ is A or G; $X_{5u}$ is A or G; $X_{6u}$ is I or C; $X_{7u}$ is I or A; $X_{8u}$ is I or G; $X_{9u}$ is C or T; $X_{10u}$ is A or G;
$X_{1d}$ is I or C; $X_{2d}$ is I or T; $X_{3d}$ is I or G; $X_{4d}$ is A or G; $X_{5d}$ is I or G; $X_{6d}$ is I or G; $X_{7d}$ is C or T; and $X_{8d}$ is C or T; and
wherein the polynucleotide corresponds to a portion of an archaea thermosome polynucleotide.

The polynucleotide formula provided encompasses for example, isolated nucleic acids useful for example as probes for detecting archaea thermosome polynucleotide target sequence, JH0175/JH0178 primers and JH0268/JH0269 primers as well as primers with specific nucleotides for degenerate positions in JH0175 and/or JH0178, e.g. where M=A or C, and primers where one or more of the degenerate nucleotides in JH0175 and/or JH0178 is/are replaced with a specific nucleotide base found in a high G+C archaea organism. The isolated nucleic acids and/or polynucleotide primers can for example specifically hybridize to an archaea thermosome polynucleotide target sequence, for example at a specific annealing temperature in a PCR reaction and/or under stringent hybridization conditions.

In an embodiment, the isolated nucleic acid molecule comprises:
 a) a polynucleotide comprising at least 10 contiguous nucleotides of: GGI CCI MRR GGI ITI GAY AAR ATG (SEQ ID NO:3), GCI AII TCR TCI ATI CCY TTY TG (SEQ ID NO:4), GGC CCG AAG GGC ATG GAC AAG ATG (SEQ ID NO:5) or GCC ATG TCG TCG ATG CCC TTC TG (SEQ ID NO:6);
 b) a polynucleotide having at least 80% sequence identity to: GGI CCI MRR GGI ITI GAY AAR ATG (SEQ ID NO:3), GCI AII TCR TCI ATI CCY TTY TG (SEQ ID NO:4), GGC CCG AAG GGC ATG GAC AAG ATG (SEQ ID NO:5) or GCC ATG TCG TCG ATG CCC TTC TG (SEQ ID NO:6); or
 c) a polynucleotide reverse complementary to a) or b).

In an embodiment, the disclosure provides a mixture of isolated nucleic acid molecules comprising two or more isolated nucleic acid molecules or polynucleotide primers according to a polynucleotide formula described herein. In an embodiment the mixture is a mixture of thermosome polynucleotide probes comprising two or more of SEQ ID NOs: 1 to 6. The mixture in an embodiment, comprises 2, 4, 6, 16, 32, 64, 128, 256, 512, 1024 isolated nucleic acid molecules or polynucleotide primers. In an embodiment, the mixture comprises two or more isolated nucleic acid molecules or polynucleotide primers according to anyone of SEQ ID NOs:1-6 or combinations thereof. The sequences specified by the SEQ ID NOs: 1 to 6, include positions with 2 fold degeneracy e.g. specified by M, R and Y. An isolated nucleic acid molecule or polynucleotide primer comprising a sequence of SEQ ID NO:3 can specify for example 32 different sequences as SEQ ID NO:3 comprises 5 positions with 2 fold degeneracy (e.g. which can be 2 different bases at a particular position). For example, positions where 2 different nucleotides (like Y=C+T) can be specified, the polynucleotide can be synthesized by using both nucleotides e.g. C and T, for the particular position (for example C and T can be in equal ratios), providing a mixture of nucleic acids or primers having where Y is specified with either a C or a T at the particular position. Where for example equal ratios of C and T are provided, approximately half of the nucleic acids or primers will have a C and approximately half will have a T at a position specified by Y. The more degenerate positions in a sequence, the more possible combinations of nucleic acids/primers. For example, JH0175 (SEQ ID NO:3) has 5 positions with 2-fold degeneracy. When JH0175 primer is synthesized, there will be mixes as 2×2×2×2×2 positions equaling 32 possible combinations. Accordingly, JH0175 (SEQ ID NO:3) comprises a mixture of 32 different, specific primers. Similarly as SEQ ID NO:1 comprises 10 degenerate positions, a mixture comprising isolated nucleic acids comprising SEQ ID NO:1 can include 1024 different sequences. Further, for example mixtures of SEQ ID NO: 1 and 2 can comprise mixtures comprising 1024+256 nucleic acid molecules. In an embodiment, the mixture comprises about equal concentrations of each of the polynucleotides defined by for example SEQ ID NO:1, 2, 3, 4, 5 or 6.

In an embodiment, the mixture comprises isolated nucleic acid molecules comprising sequences selected from SEQ ID NOs:1 and 2; SEQ ID NOs: 3 and 4; or SEQ ID NOs: 5 and 6.

The sequences include for example inosine or "I" nucleotide analogs.

As used herein, "I" represents inosine, a nucleotide analog with the property of base pairing with any nucleotide. Inosine residues are included to reduce primer degeneracy created by accommodating highly variable positions (for example, where all 4 nucleotides occur with equal or nearly equal frequency).

In an embodiment, one or more "I" nucleotides are replaced with G, T, C or A for example for designing more focused primers that amplify a subset or archaea. Similarly "I" can be replaced with other nucleoside analogs.

As used herein, "M" represents the International Union of Pure and Applied Chemistry (IUPAC) code for nucleotides A and C. Accordingly, each "M" nucleotide can independently be A or C.

The nucleotide "R" represents the International Union of Pure and Applied Chemistry (IUPAC) code for nucleotides A and G. Accordingly, each "R" nucleotide can independently be A or G.

The nucleotide "Y" represents the International Union of Pure and Applied Chemistry (IUPAC) code for C and T. Accordingly, each "Y" nucleotide can independently be C or T.

The term "polynucleotide", "nucleic acid", "nucleic acid molecule" and/or "oligonucleotide" as used herein refers to a sequence of nucleotide or nucleoside monomers consisting of naturally occurring and/or modified bases, sugars, and inter-sugar (backbone) linkages, and is intended to include DNA and RNA which can be either double stranded or single stranded, representing the sense or antisense strand.

As used herein, the term "isolated nucleic acid molecule" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

The term "sequence identity" as used herein refers to the percentage of sequence identity between two or more polypeptide sequences or two or more nucleic acid sequences that have identity or a percent identity for example about 70% identity, 80% identity, 90% identity, 95% identity, 98% identity, 99% identity or higher identity or a specified region. To determine the percent identity of two or more amino acid sequences or of two or more nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). The percent identity between two sequences can be determined using techniques similar to those described above, with or without allowing gaps. In calculating percent identity, typically only exact matches are counted.

The term "reverse complement" or "reverse complementary", when referring to a polynucleotide, as used herein refers to a polynucleotide comprising a sequence that is complementary to a DNA in terms of base-pairing and which is reversed so oriented from the 5' to 3' direction.

In an embodiment, the isolated nucleic acid is suitable for use as a polynucleotide primer.

In an embodiment, the isolated nucleic acid molecule comprises a polynucleotide comprising at least 10, 11, 12, 13, 14, 15, 16, 17, 18, 19, 20, 21, 22, 23 or 24 contiguous nucleotides of any one of SEQ ID NOs:1 to 6. In another embodiment, the polynucleotide is from about 10 to 23 nucleotides in length. In another embodiment, the polynucleotide is from about 10 to 24 in length.

In an embodiment, the isolated nucleic acid molecule comprises a polynucleotide described herein and a linker. In an embodiment, the linker is a "T" or an "A" nucleotide which can be used for example with TA plasmids for recombinantly propagating an amplified polynucleotide. For example, the restriction enzyme linker can be 4, 5, 6 or more nucleotides in length. Accordingly, in an embodiment, the isolated nucleic acid molecule is from about 14 to about 30 nucleotides and the isolated nucleic acid molecule comprises a linker, such as a restriction enzyme linker at a 5' end of the polynucleotide for example at a 5' end of a polynucleotide comprising at least 10 contiguous nucleotides of any one of SEQ ID NOs: 1 to 6.

The term "restriction enzyme linker" as described herein refers to a polynucleotide sequence which comprises a restriction enzyme recognition site for example an EcoRI site, BamHI site, HindIII site, PvuII site, etc, as would be known to a person skilled in the art.

In an embodiment, the restriction enzyme linker when double stranded comprises an overhang sequence, wherein an "overhang sequence" refers to one or more unpaired nucleotides at the end of a double stranded DNA molecule. In another embodiment, the restriction enzyme linker comprises a blunt end, wherein a "blunt end" refers to an end of a double stranded polynucleotide wherein both nucleic acid strands terminate with bases paired.

The isolated nucleic acids can be useful as polynucleotide primers for amplifying an archaea thermosome polynucleotide target. The amplification of the target polynucleotide for example produces an isolated nucleic acid molecule or mixture of isolated nucleic acid molecules, useful for example as probes as the isolated nucleic acid molecule corresponds to and/or is reverse complementary to an archaea thermosome polynucleotide target. In an embodiment the isolated nucleic acid comprises from 10 to 750 nucleotides, from 10 to 700 nucleotides, from 10 to 600 nucleotides, from 10 to 500 nucleotides, from 10 to 400 nucleotides, from 10 to 300 nucleotides or from 10 to 200 nucleotides or any number between 10 and 750 nucleotides. For example, the nucleotide sequence of the probe corresponds to and/or is a reverse complement to an archaea thermosome polynucleotide, the sequence of which can be determined for example by sequence analysis as known in the art.

In another embodiment, the isolated nucleic acid molecule comprises from about 100 to about 700 nucleotides, from 100 to 600 nucleotides, from 100 to 500 nucleotides, from 100 to 400 nucleotides, from 100 to 300 nucleotides or from 100 to 200 nucleotides.

In an embodiment, the isolated nucleic acid molecule is a PCR product amplified using a polynucleotide primer set disclosed herein.

In an embodiment, the isolated nucleic acid molecule and/or polynucleotide is labeled and/or comprises a label. The label is preferably capable of producing, either directly or indirectly, a detectable signal. For example, the label may be radio-opaque or a radioisotope, such as $^3$H, $^{14}$C, $^{32}$P; a fluorescent (fluorophore) or chemiluminescent (chromophore) compound, such as rhodamine; an enzyme, such as alkaline phosphatase, or horseradish peroxidase; an imaging agent; or a metal ion. Different isolated nucleic acid molecules or primers can be labeled with different labels.

Accordingly, in another embodiment, the isolated nucleic acid molecule comprises a polynucleotide comprising at least 10 contiguous nucleotides of: SEQ ID NO:1, SEQ ID NO:2, GGI CCI MRR GGI ITI GAY AAR ATG (SEQ ID NO:3), GCI AII TCR TCI ATI CCY TTY TG (SEQ ID NO:4), GGC CCG AAG GGC ATG GAC AAG ATG (SEQ ID NO:5) or GCC ATG TCG TCG ATG CCC TTC TG (SEQ ID NO:6), wherein the isolated nucleic acid molecule and/or polynucleotide comprises a label and/or is labeled.

For example, labeled isolated nucleic acids can be used for in situ hybridization. In this technique a primer/probe is labeled and contacted with for example a fixed tissue under suitable environment wherein the label permits visualization of the presence or absence of a polynucleotide target and a corresponding organism spatially in the sample. For example, this technique could highlight that an organism is inside a specific cell type or that 2 different organisms are always found close together is symbiosis.

As mentioned, the nucleic acid molecules are useful as primers for amplifying an archaea thermosome polynucleotide. "Amplifying an archaea polynucleotide" as used herein refers to production of multiple copies of a sequence of DNA, e.g. a portion of an archaea thermosome genomic DNA sequence or a portion of an archaea thermosome cDNA sequence. For example, primers are provided herein which can be used to amplify a portion (e.g. about 750 nucleotides) of archaea thermosome DNA.

Accordingly, in another aspect, the disclosure includes a set of polynucleotide primers for amplifying an archaea thermosome polynucleotide, the primer set comprising:
  a) one or more upstream primers comprising a polynucleotide comprising at least 10 contiguous nucleotides of: GGX$_{1u}$ CCX$_{2u}$ X$_{3u}$X$_{4u}$X$_{6u}$ GGX$_{6u}$ X$_{7u}$TX$_{8u}$ GAX$_{9u}$ AAX$_{10u}$ ATG (SEQ ID NO:1); and one or more downstream primers comprising a polynucleotide comprising at least 10 contiguous nucleotides of: GCX$_{1d}$ AX$_{2d}$X$_{3d}$ TCX$_{4d}$ TCX$_{5d}$ ATX$_{6d}$ CCX$_{7d}$ TTX$_{5d}$ TG (SEQ ID NO:2); or
  b) one or more upstream primers comprising a polynucleotide comprising at least 10 contiguous nucleotides of a sequence reverse complementary to: GGX$_{1u}$ CCX$_{2u}$ X$_{3u}$X$_{4u}$X$_{5u}$ GGX$_{6u}$ X$_{7u}$TX$_{8u}$ GAX$_{9u}$ AAX$_{10u}$ ATG (SEQ ID NO:1); and one or more downstream primers comprising a polynucleotide comprising at least 10 contiguous nucleotides of a sequence reverse complementary to: GCX$_{1d}$ AX$_{2d}$X$_{3d}$ TCX$_{4d}$ TCX$_{5d}$ ATX$_{6d}$ CCX$_{7d}$ TTX$_{8d}$ TG (SEQ ID NO:2).

wherein
  X$_{1u}$ is I or C; X$_2$, is I or G; X$_{3u}$ is A or C; X$_{4u}$ is A or G; X$_{5u}$ is A or G; X$_{6u}$ is I or C; X$_{7u}$ is I or A; X$_{8u}$ is I or G; X$_{9u}$ is C or T; X$_{10u}$ is A or G;
  X$_{1d}$ is I or C; X$_{2d}$ is I or T; X$_{3d}$ is I or G; X$_{4d}$ is A or G; X$_{5d}$ is I or G; X$_{6d}$ is I or G; X$_{7d}$ is C or T; and X$_{8d}$ is C or T.

In an embodiment, the primer set comprises:
  a) one or more upstream primers comprising a polynucleotide comprising at least 10 contiguous nucleotides of: GGI CCI MRR GGI ITI GAY AAR ATG (SEQ ID NO:3) or GGC CCG AAG GGC ATG GAC AAG ATG (SEQ ID NO:5); and one or more downstream primers comprising a polynucleotide comprising at least 10 contiguous nucleotides of: GCI AII TCR TCI ATI CCY TTY TG (SEQ ID NO:4) or GCC ATG TCG TCG ATG CCC TTC TG (SEQ ID NO:6); or
  b) one or more upstream primers comprising a polynucleotide comprising at least 10 contiguous nucleotides of a sequence complementary to: GGI CCI MRR GGI ITI GAY MR ATG (SEQ ID NO:3) or GGC CCG MG GGC ATG GAC MG ATG (SEQ ID NO:5); and one or more downstream primers comprising a polynucleotide comprising at least 10 contiguous nucleotides of a sequence complementary to: GCI AII TCR TCI ATI CCY TTY TG (SEQ ID NO:4) or GCC ATG TCG TCG ATG CCC TTC TG (SEQ ID NO:6).

In an embodiment, the upstream and/or downstream primer comprises a polynucleotide comprising at least 10, 11, 12, 13, 14, 15, 16, 17, 18, 19, 20, 21, 22, 23 or 24 contiguous nucleotides. In another embodiment, the polynucleotide is from about 10 to about 23 nucleotides in length. In another embodiment, the polynucleotide is about 10 to 24 nucleotides in length.

In an embodiment, the one or more upstream primers and/or downstream primers comprise a polynucleotide described herein and a linker such as a restriction enzyme linker as described herein. In an embodiment, the one or more upstream primers and/or downstream primers comprise a restriction enzyme linker at a 5' end of the polynucleotide.

For example, the restriction enzyme linker can be 4, 5, 6 or more nucleotides in length. Accordingly, in an embodiment, the one or more upstream primers and/or downstream primers comprise from about 14 to about 30 nucleotides in length.

In an embodiment, the primer set comprises one or more upstream and/or downstream primers, wherein the one or more upstream and/or downstream primers are labeled. Accordingly, in an embodiment the primer set comprises:
  a) one or more upstream primers comprising a polynucleotide comprising at least 10 contiguous nucleotides of: SEQ ID NO:1, GGI CCI MRR GGI ITI GAY AAR ATG (SEQ ID NO:3), GGC CCG AAG GGC ATG GAC MG ATG (SEQ ID NO:5); and
  b) one or more downstream primers comprising a polynucleotide comprising at least 10 contiguous nucleotides of: SEQ ID NO:2. GCI AII TCR TCI ATI CCY TTY TG (SEQ ID NO:4), or GCC ATG TCG TCG ATG CCC TTC TG (SEQ ID NO:6);

wherein the one or more upstream primers and/or polynucleotides and/or one or more downstream primers comprises a label and/or is/are labeled.

The term "primer" as used herein refers to a nucleic acid molecule, whether occurring naturally as in a purified restriction digest or produced synthetically, which is capable of acting as a point of synthesis of when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less, for example 10 nucleotides. The factors involved in determining the appropriate length of primer are readily known to one of ordinary skill in the art. Where a primer includes degenerate positions e.g. Y, M or R, the primer can for example comprise a mixture of polynucleotides dictated by the degenerate positions or a subset thereof.

The term "primer set" as used herein refers to a set of primers that hybridize specifically to a polynucleotide. Each primer set comprises two or more polynucleotide primers, for example 2, 3, 4, or more primers, and can include at least one upstream and one downstream primer. For example, a primer set can include, a primer pair comprising an upstream and a downstream primer and/or multiple primer pairs comprising more than one upstream and more than one downstream primer. The term "primer pair" as used herein refers to 2 primers, an upstream primer and a downstream primer which are used to amplify a specific polynucleotide.

As used herein, the term "upstream primer" as used herein refers to a primer that can hybridize to a DNA sequence and act as a point of synthesis upstream, or at a 5', of a target polynucleotide sequence, to produce a polynucleotide complementary to the target polynucleotide anti-sense strand. The term "downstream primer" as used herein refers to a primer that can hybridize to a polynucleotide sequence and act as a point of synthesis downstream, or at a 3' end, of a target polynucleotide sequence, to produce a polynucleotide complementary to the target polynucleotide sense strand.

As used herein, the term "archaea thermosome target polynucleotide sequence" or interchangeably "archaea thermosome polynucleotide target" refers to a polynucleotide or part thereof of interest, that is for example to be amplified using a primer set disclosed herein. The polynucleotide target can be any archaea thermosome polynucleotide for which its determination and/or detection is indicative, associated or representative of the presence of archaea. The polynucleotide target can include for example a DNA target such as a genomic DNA target. For example, the thermosome primers disclosed herein bind to positions corresponding to positions 145-168 and 895-917 from the *Nanoarchaeum equitans* Kin4-M thermosome polynucleotide gene sequence. The numbering is different for each species and in general, the target is from about by positions 150-900 of the archaea species thermosome gene, which is approximately 750 nucleotides in length depending on the species. The DNA target can also be for example a cDNA target.

In an embodiment, the archaea thermosome polynucleotide target is an archaea thermosome DNA target.

As used herein "archaea thermosome polynucleotide" refers to polynucleotide sequences of the archaea type II chaperonin gene which is known as thermosome, TF55, CCT or TCP-1, and includes genomic, cDNA and mRNA sequences. The polynucleotide sequence of archaea thermosome gene varies between species and genera. Exemplary thermosome polynucleotide sequences include those deposited in Genbank with Accession numbers NC_013790, AF010469, NC_000868 and NC_014820. Sequences described throughout by accession, including NC_013790, AF010469, NC_000868 and NC_014820 are herein incorporated by reference.

In an embodiment, the one or more upstream primers comprises a polynucleotide consisting of GGI CCI MRR GGI ITI GAY AAR ATG (SEQ ID NO:3) or GGC CCG MG GGC ATG GAC MG ATG (SEQ ID NO:5); and the one or more downstream primers comprise a polynucleotide consisting of GCI AII TCR TCI ATI CCY TTY TG (SEQ ID NO:4) or GCC ATG TCG TCG ATG CCC TTC TG (SEQ ID NO:6).

In an embodiment, the upstream primer comprises a polynucleotide consisting of GGI CCI MRR GGI ITI GAY MR ATG (SEQ ID NO:3); and the downstream primer comprises a polynucleotide consisting of GCI AII TCR TCI ATI CCY TTY TG (SEQ ID NO:4).

In another embodiment, the upstream primer comprises a polynucleotide consisting of the reverse complement of GGI CCI MRR GGI ITI GAY AAR ATG (SEQ ID NO:3); and the downstream primer comprises a polynucleotide consisting of the reverse complement of GCI AII TCR TCI ATI CCY TTY TG (SEQ ID NO:4).

In an embodiment, the upstream primer comprises a polynucleotide consisting of GGI CCI MRR GGI ITI GAY AAR ATG (SEQ ID NO:3), and the downstream primer comprises a polynucleotide consisting of GCC ATG TCG TCG ATG CCC TTC TG (SEQ ID NO:6).

In another embodiment, the upstream primer comprises a polynucleotide consisting of the reverse complement of GGI CCI MRR GGI ITI GAY AAR ATG (SEQ ID NO:3), and the downstream primer comprises a polynucleotide consisting of the reverse complement of GCC ATG TCG TCG ATG CCC TTC TG (SEQ ID NO:6).

In an embodiment, the upstream primer comprises a polynucleotide consisting of GGC CCG MG GGC ATG GAC MG ATG (SEQ ID NO:5), and the downstream primer comprises a polynucleotide consisting of GCI AII TCR TCI ATI CCY TTY TG (SEQ ID NO:4).

In another embodiment, the upstream primer comprises a polynucleotide consisting of the reverse complement of GGC CCG AAG GGC ATG GAC AAG ATG (SEQ ID NO:5), and the downstream primer comprises a polynucleotide consisting of the reverse complement of GCI AII TCR TCI ATI CCY TTY TG (SEQ ID NO:4).

An upstream primer can for example be paired with a downstream primer. A person skilled in the art would understand that a primer that comprises a reverse complement sequence of for example an upstream primer such as SEQ ID NO:1, 3 or 5, would be paired with a primer that comprises a reverse complement sequence of a downstream primer such as SEQ ID NO:2, 4 or 6.

In an embodiment, the upstream primer comprises a polynucleotide consisting of GGC CCG AAG GGC ATG GAC AAG ATG (SEQ ID NO:5), and the downstream primer comprises a polynucleotide consisting of GCC ATG TCG TCG ATG CCC TTC TG (SEQ ID NO:6).

In another embodiment, the upstream primer comprises a polynucleotide consisting of the reverse complement of GGC CCG AAG GGC ATG GAC AAG ATG (SEQ ID NO:5), and the downstream primer comprises a polynucleotide consisting of the reverse complement of GCC ATG TCG TCG ATG CCC TTC TG (SEQ ID NO:6).

In an embodiment, one of the one or more upstream primers comprises the polynucleotide consisting of GGI CCI MRR GGI ITI GAY AAR ATG (SEQ ID NO:3) and another of the one or more upstream primers comprises the polynucleotide consisting of GGC CCG AAG GGC ATG GAC MG ATG (SEQ ID NO:5), and one of the one or more downstream primers comprises a polynucleotide consisting of GCI AII TCR TCI ATI CCY TTY TG (SEQ ID NO:4) and another of the one or more downstream primers comprises a polynucleotide consisting of GCC ATG TCG TCG ATG CCC TTC TG (SEQ ID NO:6).

In another embodiment, one of the one or more upstream primers comprises the polynucleotide consisting of the reverse complement of GGI CCI MRR GGI ITI GAY AAR ATG (SEQ ID NO:3) and another of the one or more upstream primers comprises the polynucleotide consisting of the reverse complement of GGC CCG AAG GGC ATG GAC AAG ATG (SEQ ID NO:5), and one of the one or more downstream primers comprises a polynucleotide consisting of the reverse complement of GCI AII TCR TCI ATI CCY TTY TG (SEQ ID NO:4) and another of the one or more downstream primers comprises a polynucleotide consisting of the reverse complement of GCC ATG TCG TCG ATG CCC TTC TG (SEQ ID NO:6).

In an embodiment, each the upstream and/or downstream primers described herein is about 30 nucleotides in length. For example, the upstream and/or downstream primer comprises a polynucleotide described herein and a restriction enzyme linker for example to aid in recombinant DNA methods for propagating the isolated nucleic acid molecule. Accordingly, in an embodiment, the upstream and/or downstream primer described herein is about 30 nucleotides in length and the upstream and/or downstream primer comprises a restriction enzyme linker at a 5' end of the polynucleotide.

In an embodiment, the upstream and/or downstream primer described herein comprises a polynucleotide described herein, wherein the upstream and/or downstream primer is labeled.

In an aspect, the disclosure includes a set of polynucleotide primers for amplifying an archaea thermosome polynucleotide, the primer set comprising multiple primer pairs, each primer pair comprising an upstream primer and a downstream primer. For example, the primer set can include 2 or more upstream primers each comprising a polynucleotide comprising at least 10 contiguous nucleotides of SEQ ID NO:1 and two or more downstream primers each comprising a polynucleotide comprising at least 10 contiguous nucleotides of SEQ ID NO:2. (e.g. each upstream primer having a different selection of nucleotides for variable positions and each downstream primer having a different selection of nucleotides for variable positions). In an embodiment, the primer set comprises two or more upstream primers each comprising a reverse complementary polynucleotide of at least 10 nucleotides of SEQ ID NO:1 and two or more downstream primers each comprising a reverse complementary polynucleotide of at least 10 nucleotides of SEQ ID NO:1. In another embodiment, the primer set comprises combinations of primer pairs (e.g. primer pairs derived from SEQ ID NO:1 and 2 and reverse complementary primers derived from SEQ ID NO:1 and 2).

In an embodiment, the primer set comprises a first primer pair comprising an upstream primer described herein for example comprising a polynucleotide consisting of GGI CCI MRR GGI ITI GAY AAR ATG (SEQ ID NO:3) and a downstream primer described herein for example comprising a polynucleotide consisting of GCI AII TCR TCI ATI CCY TTY TG (SEQ ID NO:4) and a second primer pair comprising an upstream primer comprising a polynucleotide consisting of GGC CCG AAG GGC ATG GAC AAG ATG (SEQ ID NO:5) and a downstream primer comprising a polynucleotide consisting of GCC ATG TCG TCG ATG CCC TTC TG (SEQ ID NO:6). In another embodiment, the primer set comprises: a first primer pair comprising a polynucleotide consisting of the reverse complement of GGI CCI MRR GGI ITI GAY AAR ATG (SEQ ID NO:3) and a polynucleotide consisting of the reverse complement of GCI AII TCR TCI ATI CCY TTY TG (SEQ ID NO:4) and a second primer pair comprising a polynucleotide consisting of the reverse complement of GGC CCG AAG GGC ATG GAC MG ATG (SEQ ID NO:5) and a polynucleotide consisting of the reverse complement of GCC ATG TCG TCG ATG CCC TTC TG (SEQ ID NO:6).

Where the primer set comprises multiple primer pairs, e.g. a first primer pair and second primer pair, the primer pairs can be provided at particular ratio, e.g. a ratio of the first primer pair to the second primer pair. Accordingly, in an aspect, the disclosure includes a set of polynucleotide primers for amplifying an archaea thermosome polynucleotide, the primer set comprising: a first primer pair and a second primer pair wherein the ratio of the first primer pair to the second primer pair is about 1:1. In another embodiment, the ratio of the first primer pair to the second primer pair is about 2:1 or about 3:1. In another embodiment, the ratio of the first primer pair to the second primer pair is about 1:7, 1:3, 1:1, 3:1, 7:1, 15:1, 31:1, 63:1, 127:1 and 255:1 or any ratio between 1:7 and 255:1

For example to get the most universal amplification of all possible archaea of different G+C contents, using the primers with a 7:1 ratio is suitable. When targeting high G+C organism, ratios of 1:7 to 7:1 give good amplification; when targeting low G+C organisms, ratios of 7:1 to 255:1 give good amplification. The 7:1 ratio can be used to amplify a wide range of G+C organisms.

In an embodiment, primers amplify a nucleic acid that is useful as a probe.

The term "probe" as used herein refers to a polynucleotide that comprises a sequence of nucleotides that will hybridize specifically to a target nucleic acid sequence. For example the probe comprises at least 10 or more bases or nucleotides that are complementary and hybridize to contiguous bases and/or nucleotides in the target nucleic acid sequence. The length of probe depends on the hybridization conditions and the sequences of the probe and nucleic acid target sequence and can for example be 10-20, 21-70, 71-100, 101-500 or more bases or nucleotides in length. The probes can optionally be fixed to a solid support such as an array chip or a microarray chip. For example, the PCR product produced with the primers could be used as a probe. The PCR product can be for example be subcloned into a vector and optionally digested and used as a probe. Alternatively, the primers themselves could be used as universal probes for archaea for application in techniques such as fluorescence in situ hybridization (FISH).

Accordingly, in an embodiment, the isolated nucleic acid molecule/polynucleotide/primer are fixed to a solid support. In an embodiment, the disclosure includes an array comprising isolated nucleic acid molecules, polynucleotides and/or primers disclosed herein.

In another embodiment the isolated nucleic acid molecule/polynucleotide/probe/primer is labeled with a label. In another embodiment, the label is a fluorescent marker, such as a fluorophore.

The term "specifically binds" as used herein refers to a binding reaction that is determinative of the presence of the analyte (e.g. target nucleic acid) often in a heterogeneous population of macromolecules. For example, specifically binds when referring to a probe means the specified probe or primer under suitable hybridization conditions binds to a particular nucleotide sequence or set of related nucleotide sequences at least 1.5, at least 2 or at least 3 times background.

The term "hybridize" as used herein refers to the sequence specific non-covalent binding interaction with a complementary nucleic acid. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. can be employed. With respect to a chip array, appropriate stringency conditions are known in the art.

The term "stringent hybridization conditions" refers to conditions under which a probe will hybridize to its target subsequence, typically in a complex mixture of nucleic acids, but to no other sequences or only to sequences with greater than 95%, 96%, 97%, 98%, or 99% sequence identity. Stringent conditions are for example sequence-dependent and will be different in different circumstances. Longer sequences can require higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

The term "annealing" as used herein refers to the process by which nucleotides, for example, DNA or RNA, pair by hydrogen bonds to a complementary sequence and form a double-stranded polynucleotide. For example, a DNA probe attached to a solid support for example in a microarray chip can anneal or bind to a specific DNA target sequence or set of DNA target sequences that are complementary to the DNA probe. For example, a primer can anneal to a polynucleotide during a polymerase chain reaction (PCR) when the annealing temperature and buffer conditions are suitable for base pairing to a complementary (or partially complementary polynucleotide e.g. 3' portion of the primer). The term can also refer to reformation (renaturation) of complementary strands that were separated by heat (thermally denatured).

The term "denaturation" or "denaturing" as used herein refers to the process by which double-stranded nucleic acids unwind and separate into single-stranded strands, for example, through the breaking of hydrogen bonding between the nucleotide bases. Denaturation can occur, for example, when a polynucleotide is heated, such as, for example, during PCR, or can also occur when induced by chemicals like urea.

In an embodiment, one or more of the isolated nucleic acid molecule, primer and/or probe are comprised in a composition. In an embodiment, the composition comprises a mixture of isolated nucleic acid molecules, polynucleotides, primers and/or probes. In an embodiment, the composition comprises a mixture of isolated nucleic acid molecules, polynucleotides, primers and/or probes comprising sequences selected from any one of SEQ ID NO:1 to 6, for example one or more isolated nucleic acid molecules/polynucleotides/primers selected from SEQ ID NO:1 and one or more isolated nucleic acid molecules/polynucleotides/primers selected from SEQ ID NO:2. In an embodiment, the mixture comprises each of the polynucleotides defined by SEQ ID NO:1, 2, 3, 4, 5 or 6. In an embodiment, the composition comprises about equal concentrations of each polynucleotide defined by SEQ ID NO:1, 2, 3, 4, 5 or 6. In an embodiment, the composition comprises a combination, for example a combination of two or more primers. In an embodiment, the composition comprises a suitable diluent or carrier.

In an embodiment, the primer is attached to a bead for example for use in luminex or bioplex (multiplex) assays for total archaea detection.

In another aspect, the disclosure provides a method of amplifying an archaea thermosome polynucleotide comprising:

a) providing a sample comprising at least one archaea thermosome polynucleotide target;

b) adding a primer set for amplification of the thermosome polynucleotide target(s) and c) incubating the sample under conditions and with reagents for DNA amplification;

wherein each primer is annealed to the thermosome polynucleotide target at a position enabling amplification of the thermosome polynucleotide target and a DNA polymerase amplifies the thermosome polynucleotide target.

In certain embodiments, amplification and/or detection is performed using a polynucleotide primer. In an embodiment, a primer is used for example in a labeling by synthesis reaction (e.g. linear amplification instead of exponential amplification).

In an embodiment, wherein primer corresponds to a portion of an archaea thermosome gene.

In an embodiment, amplification of an archcaea polynucleotide is diagnostic for the presence of archaea organisms.

In an embodiment, the method comprises:

a) providing a sample comprising at least one archaea thermosome polynucleotide target;

b) adding a primer set for amplification of the thermosome polynucleotide target(s) comprising: an upstream primer comprising a polynucleotide consisting of at least 10 contiguous nucleotides of SEQ ID NO:1; and a downstream primer comprising a polynucleotide consisting of SEQ ID NO:2; and c) incubating the sample under conditions and with reagents for DNA amplification wherein each primer is annealed to the thermosome polynucleotide target at a position enabling amplification of the thermosome polynucleotide target and a DNA polymerase amplifies the thermosome polynucleotide target.

In an embodiment, the primer pair comprises at least one upstream primer comprising a polynucleotide consisting of at least 10 contiguous nucleotides of SEQ ID NO:3 and/or 5 and at least one downstream primer comprising a polynucleotide consisting of at least 10 contiguous nucleotides SEQ ID NO:4 and/or 6. For example, the primer pair can comprise an upstream primer comprising at least 10 contiguous nucleotides of SEQ ID NO:3 and a downstream primer comprising at least 10 contiguous nucleotides of SEQ ID NO:6; an upstream primer comprising at least 10 contiguous nucleotides of SEQ ID NO:5 and a downstream primer comprising at least 10 contiguous nucleotides of SEQ ID NO:4; an upstream primer comprising at least 10 contiguous nucleotides of SEQ ID NO:3 and a downstream primer comprising at least 10 contiguous nucleotides of SEQ ID NO:4; and an upstream primer comprising at least 10 contiguous nucleotides of SEQ ID NO:5 and a downstream primer comprising at least 10 contiguous nucleotides of SEQ ID NO:6.

In an embodiment, the primer set comprises two or more primer pairs, for example added at a ratio described herein.

In an embodiment, the method comprises:
a) providing a sample comprising at least one archaea thermosome polynucleotide target;
b) adding a primer set for amplification of the thermosome polynucleotide target(s) comprising: an upstream primer comprising a polynucleotide consisting of SEQ ID NO:3 and another upstream primer comprising a polynucleotide consisting of SEQ ID NO:5; and a downstream primer comprising a polynucleotide consisting of SEQ ID NO:4 and another downstream primer comprising a polynucleotide consisting of SEQ ID NO:6; and
c) incubating the sample under conditions and with reagents suitable for DNA amplification.
wherein each primer is annealed to the thermosome polynucleotide target at a position enabling amplification of the thermosome polynucleotide target and a DNA polymerase amplifies the thermosome polynucleotide target.

In an embodiment, the thermosome polynucleotide target is thermosome genomic DNA.

It is demonstrated herein that the primers can be used to amplify thermosome polynucleotide targets with a range of GC contents.

As used herein, the term "G+C content" or "GC content" refers to the amount of nitrogenous bases of a particular or target DNA or RNA molecule (e.g. the target thermosome polynucleotide) that are either guanine (G) or cytosine (C) typically expressed as a percent. Where the sequence of particular DNA or RNA is known, the G+C content can be determined using the formula:

$$\frac{G+C}{A+T+G+C} \times 100$$

wherein G, C, A and T refer to the number of each residue in the particular or target DNA, to provide a percent GC content (for RNA T is substituted by U).

The G+C content can be estimated for example by taking known polynucleotide sequences from an organism (either whole genome or sequenced genes), determine the G+C content of those pieces and optionally averaging to get an estimate of the GC content. Organisms that are phylogenetically similar often have similar G+C contents, G+C content can be extrapolated known G+C contents to closely related organisms.

In an embodiment, the polynucleotide target has a G+C content of less than about 68%. In another embodiment, the polynucleotide target has a G+C content of less than about 66%. In another embodiment, the polynucleotide target has a G+C content of less than about 60%. In a further embodiment, the polynucleotide target has a G+C content of less than about 54%. In still another embodiment, the polynucleotide target has a G+C content of about 27% to about 54%. In another embodiment, the polynucleotide target has a G+C content of about 40% to about 66%. In another embodiment still, the polynucleotide target has a G+C content of about 25% to about 70%. In yet another embodiment, the polynucleotide target has a G+C content of about 27% to about 66%.

In another embodiment, the primer set comprises two or more primer pairs, described herein, for example selected from upstream primers having a sequence selected from SEQ ID NO:1 and from downstream primers having a sequence selected from SEQ ID NO:2. In an embodiment, the primer set comprises two or more primer pairs, each upstream primer comprising a polynucleotide consisting of at least 10 contiguous nucleotides of: GGI CCI MRR GGI ITI GAY AAR ATG (SEQ ID NO:3) or GGC CCG AAG GGC ATG GAC AAG ATG (SEQ ID NO:5), and each downstream primer comprising a polynucleotide consisting of: GCI AII TCR TCI ATI CCY TTY TG (SEQ ID NO:4) or GCC ATG TCG TCG ATG CCC TTC TG (SEQ ID NO:6); and the G+C content of about 25% to about 70%.

Where multiple primer pairs are added, the primers can be added in a selected ratio for example a ratio described herein.

In an embodiment, the method described herein comprises polymerase chain reaction (PCR).

Annealing temperature gradient PCR reactions have been performed as described herein using the JH0175 (SEQ ID NO:3)/JH0178 (SEQ ID NO:4) or the JH0268 (SEQ ID NO:5)/JH0269 (SEQ ID NO:6) primer pairs. Accordingly, in another embodiment, the conditions for DNA amplification comprise an annealing temperature from about 45° C. to about 58° C. In a further embodiment, the conditions for DNA amplification comprise an annealing temperature from about 48° C. to about 54° C.

A number of PCR programs can be used to amplify thermosome target polynucleotide using a primer set described herein. An example of a method of amplifying comprises:
a) denaturation at about 98° C. for example for 3 minutes;
b) greater than 30, for example 40 cycles of amplification comprising denaturation at about 98° C. for example for about 30 seconds, annealing at about 54° C. for example for about 30 seconds and extension at about 72° C. for example for about 1 minute; and
c) optionally additional extension at about 72° C. (depending for example on the polymerase) for about 10 minutes.

A person skilled in the art would readily recognize that times and temperatures may vary according to whether a thermocycler is used and the type of thermocycler employed, as well as buffer conditions and the like.

Another aspect includes a method of detecting the presence or absence of an archaea organism in a sample comprising contacting the sample with a polynucleotide probe or primer which selectively hybridizes to an archaea thermosome polynucleotide target and determining whether the nucleic acid probe or primer binds to the thermosome polynucleotide target, wherein binding is indicative of the presence of archaea organisms in the sample. In an embodiment, the hybridization is under stringent hybridization conditions; wherein the identification of a hybridizable nucleic acid fragment confirms the presence of archaea.

For example, as the isolated nucleic acid molecule, probe or primer corresponds to and/or is complementary to an archaea thermosome polynucleotide, the isolated nucleic acid molecule, probe or primer, specifically binds to a portion of an archaea thermosome gene which is diagnostic for the presence of archaea.

In an embodiment, the nucleic acid probe comprises an isolated nucleic acid described herein. In an embodiment, the nucleic acid probe comprises a primer described herein.

In an embodiment, the nucleic acid probe comprises a targeting molecule such as Digoxigenin (DIG), or comprises a radioactive label for example P32, or a fluorescent label or other label as known in the art and/or described herein.

A further aspect of the disclosure includes a method of detecting the presence or absence of an archaea organism in a sample comprising amplifying an archaea thermosome polynucleotide as described above to provide an amplified thermosome polynucleotide and detecting the amplified thermosome polynucleotide, wherein the detecting of the amplified thermosome polynucleotide is indicative of the presence of the archaea organism.

A further aspect of the disclosure includes a method of detecting the presence or absence of an archaea organism in a sample comprising hybridizing the sample or a DNA fraction thereof with a isolated nucleic acid probe or primer under stringent hybridization conditions wherein the isolated nucleic acid probe and/or primer corresponds to a portion of an archaea thermosome gene which is diagnostic for the presence of archaea. In an embodiment, the isolated nucleic acid probe or primer comprises a polynucleotide or mixture of polynucleotides selected from any one of SEQ ID NOs:1 to 6.

The term "detecting an amplified polynucleotide" as used herein refers to determining the presence or absence of the amplified polynucleotide, for example an amplified by thermosome polynucleotide, by contacting the amplified polynucleotide with a reagent that allows visualization such as ethidium bromide or other polynucleotide/DNA binding dyes and the use of electrophoresis. Methods of detecting the amplified polynucleotide can include sequencing, radioactivity detection (e.g. wherein radioactive nucleotide is used during amplification), electrophoretic and hybridization based methods.

In an embodiment, the method comprises quantitating the amplified thermosome polynucleotide. For example, the amplified polynucleotide can be quantified using for example real time PCR which amplifies and allows for real time quantification and/or comparative quantification.

In another embodiment, the method comprises real time PCR, northern analysis, or hybridization assay based on oligonucleotide-coupled fluorescent microspheres. In another embodiment, the method comprises real time PCR and the amplified thermosome polynucleotide is detected and quantitated by real-time analysis.

In an aspect, the disclosure includes a method of quantifying a concentration of one or more species (and/or subspecies or genera) of an archaea organism comprising quantitatively amplifying an archaea thermosome polynucleotide using primer sets described herein and/or using species-specific primers that hybridize to sequences within the portion of the thermosome gene amplified by the primer sets described herein, and comparing the amount of amplified thermosome polynucleotide to a quantitative standard or for example using real time PCR. For example, determining the concentration of the amplified region can be used to calculate the approximate number of organisms, by comparing to a quantitative standard or quantitative standard curve. For example, a "quantitative standard" can refer to a standard or standard curve that is generated by using multiple dilutions of a known amount of standard DNA, for example a known quantity of a 750 nucleotide polynucleotide for comparing to amplified thermosome target polynucleotide or a known amount of polynucleotides that corresponds to a number of archaea organisms. The standard will depend on the method and whether a concentration of the polynucleotide is desired e.g. weight/volume, or an estimate of the archaea numbers is desired. For example, when quantitation has been determined using real time PCR, amounts of DNA that have undergone real time PCR are determined by comparing the PCR results to a standard curve produced by performing real-time PCR of serial dilutions (e.g. undiluted, 1:4, 1:16, 1:64) of a known amount of DNA.

Another aspect of the disclosure includes a method for identification of a species of an archaea organism comprising:
  a) amplifying an archaea thermosome polynucleotide as described herein to provide an amplified thermosome polynucleotide;
  b) determining the amplified thermosome polynucleotide sequence; and
  c) identifying the species of the organism.

"Determining polynucleotide sequence" can for example, comprise electrophoresis-based sequencing technology (e.g. chain termination methods, dye-terminator sequencing), by hybridization, mass spectrometry based sequencing, sequence-specific detection of single-stranded DNA using engineered nanopores and sequencing by ligation. It can also include, for example, DNA sequencing by synthesis (SBS) approaches such as pyrosequencing, sequencing of single DNA molecules and polymerase colonies.

The species of the organism is identified for example by comparing the sequence of the amplified region to the corresponding sequence of one or more known species and identifying the percent sequence identity between the amplified region, or a portion thereof.

Identifying the species of an archaea organism permits for the phylogenetic relationship of the organism to other archaea prokaryotes to be assessed. Accordingly, a further aspect of the disclosure includes a method of determining a phylogenetic relationship of a test archaea organism (e.g. a known or unknown archaea organism species) comprising:
  a) amplifying an archaea thermosome polynucleotide of the test archaea organism as described herein;
  b) determining the amplified thermosome polynucleotide sequence; and
  c) comparing the amplified thermosome polynucleotide sequence to one or more corresponding thermosome nucleotide sequences of known archaea species;
wherein the phylogenetic relationship is determined by sequence similarity to the one or more known archaea species.

In an embodiment, the method first comprises providing a polynucleotide sample comprising for example DNA, optionally a DNA fraction, comprising an archaea thermosome polynucleotide. For example, the polynucleotide sample and/or DNA can for example be a crude preparation (e.g. partially purified) or purified. A number of methods can be used to purify polynucleotides and/or DNA including various commercially available kits and reagents, combinations of mechanical and chemical disruption including bead-beating, freeze-thaw cycles, enzymatic digestion (proteinase K, lysozyme, etc.), organic solvent extraction, ethanol precipitation, removal of RNA. The DNA can be obtained from an isolate of the organism and/or be isolated from a complex sample.

A further aspect includes use of a thermosome gene as a universal amplification target for the detection, quantitation, and/or identification of one or more archaea organisms.

The methods and uses described herein have a number of applications such as testing archaeal consortia in anaerobic digestors, testing human and mammal intestinal contents, including for example cattle rumen contents, or testing soil and water samples in temperate, high salt, high pressure or high temperature conditions. In an embodiment, the sample is taken from an anaerobic digestor. The sample can for example be any sample where archaea organisms are expected to be present.

Anaerobic digestion involves for example, microorganisms breaking down biodegradable material in the absence of oxygen. Anaearobic digestors are used for industrial or domestic purposes for example to manage waste and/or to release energy.

Methane-forming archaea (methanogens) can be involved in the process of anaerobic digestion including methane-forming archaea (methanogens).

It has been found, using primer pair consisting of SEQ ID NO.3/SEQ ID NO.4 that archaea sequences from anaerobic digestors can be amplified. Profiles of productive archaea communities that enhance biogas production in anaerobic digestors can be determined and used for example to modify unproductive digestors to produce more biogas.

Accordingly a further aspect includes a method to monitor biofouling comprising detecting the presence or absence of an archaea organism in a sample, according to a method described herein, optionally identifying the species and/or quantitating one or more archaea organisms in the sample and comparing the sample to a subsequent sample, wherein an increase in the amount of archaea organisms and/or the presence of one or more species of archaea organism in the subsequent sample, is indicative of biofouling.

In an embodiment, the archaea organism that is being detected, identified and/or quantified can be comprised in a sample, for example a complex sample.

In an embodiment, the sample is a clinical sample.

In another embodiment, the sample comprises rumen and/or intestinal contents.

In an embodiment, the rumen contents are obtained from a cow, cattle, goat, sheep, bison or deer. In an embodiment, the sample comprises human intestinal contents.

In an embodiment, the sample is an environmental sample. In an embodiment, the sample is a soil sample. In another embodiment, the sample is a water sample obtained from an industrial water system. In another embodiment, the sample is a sample obtained from a gas pipeline. In an embodiment, the sample is obtained from an anaerobic digestor.

In an embodiment, the archaea organism comprises an isolated colony.

In another embodiment, the archaea organism is detected, identified and/or quantified for assessing animal nutrition and/or animal health.

In another embodiment, the archaea organism is detected, identified and/or quantified for managing waste from ruminants.

In a further aspect, the disclosure includes a method of assessing a test substance for its effect on gastrointestinal archaea makeup in a subject comprising:
  a) obtaining a first sample comprising archaea organisms from the subject;
  b) administering the test substance;
  c) obtaining a second sample comprising archaea organisms from the subject, subsequent to administration of the test substance;
  d) identifying the archaea organisms species according to a method described herein and quantifying the concentration of each species of archaea organisms in the first and second samples according to a method described herein;
wherein a difference in the archaea species and/or a difference in the concentration of one or more species are indicative that the test substance has effect on gastrointestinal archaea makeup in the subject.

The term "subject" as used herein refers to any member of the animal kingdom.

In an embodiment, the first sample is compared to a subsequent sample, e.g. a second, third etc sample obtained subsequent to the first sample.

In an embodiment, a first and a subsequent sample comprising archaea organisms are obtained from a subject, wherein the first sample is obtained before the subject has received a test substance and a subsequent sample is obtained after the subject has received a test substance. Uses are also contemplated.

Figure 2:
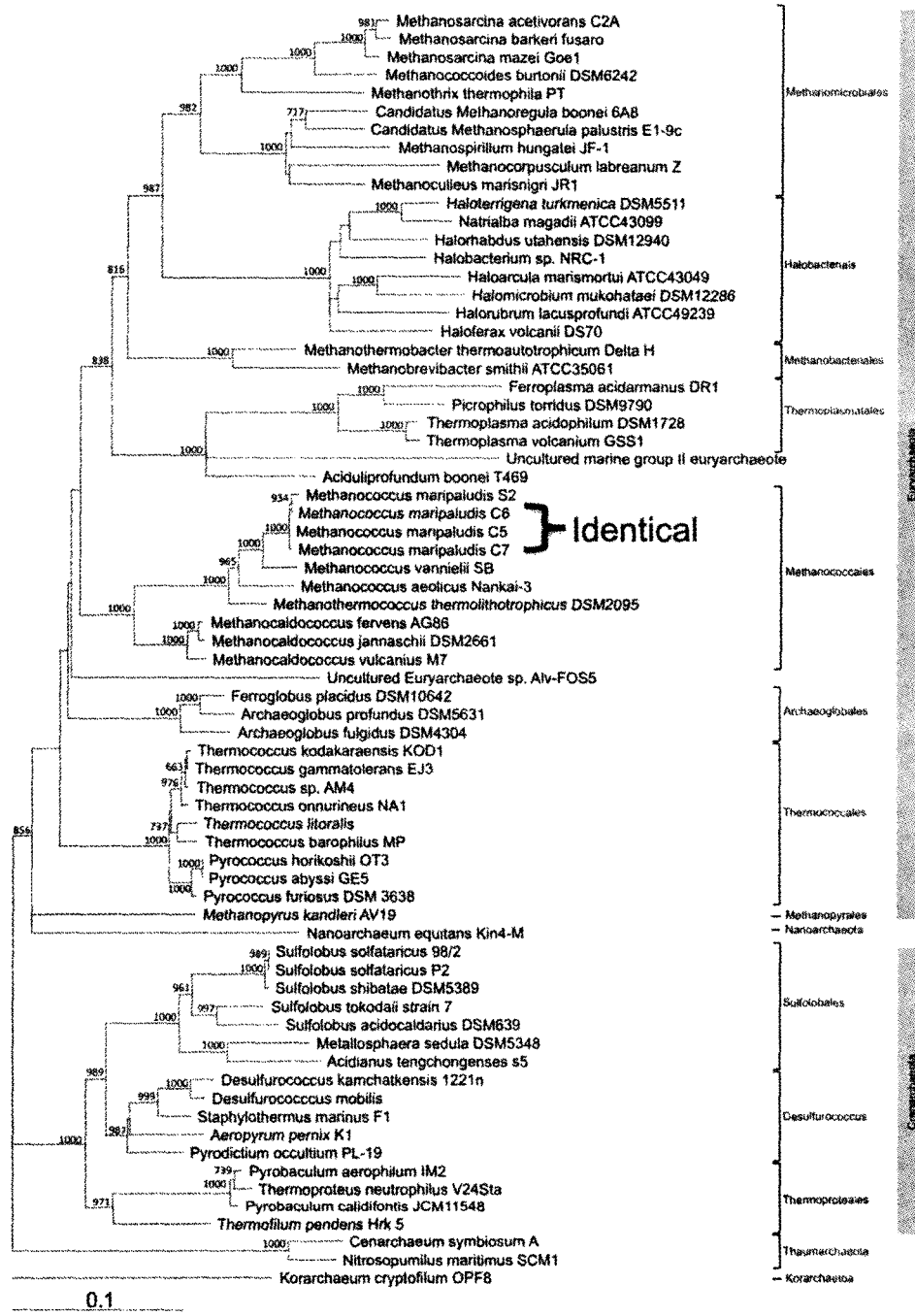
FIG. 2. Phylogenetic tree of archaeal full-length 16S rRNA genes.
Figure 9:
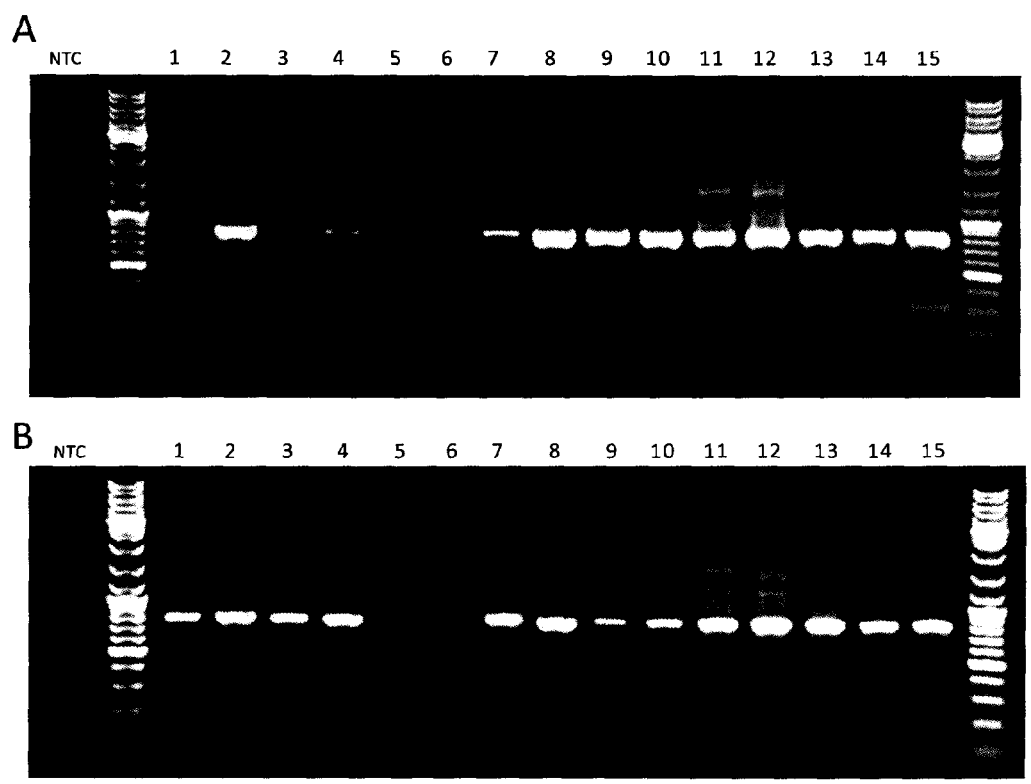
FIG. 9 (A) PCR of archaeal genomic DNA using primers mixed at ratios of 1:1 (A) and 3:1 (B) of JH0175/JH0178: JH0268/JH0269 (SEQ ID NO:3/4:SEQ ID NO:5/6). Lanes indicate (NTC) PCR no template control.; (1) *Methanococcus voltae* (27% G+C); (2) *Halobacterium salinarum* (formerly *Halobacterium halobium*) (66% G+C); (3) *Methanococcus vannielii* (31% G+C); (4) *Methanococcus maripaludis* (33%); (5) *Methanotorris igneus* (38% G+C); (6) *Sulfolobus solfataricus* (36% G+C); (7) *Sulfolobus* sp. (33-36% G+C); (8) *Thermoplasma acidophilum* (46% G+C); (9) *Halobacterium salinarum* ATCC33170 (66% G+C); (10) *Halobacterium salinarum* ATCC33171 (66% G+C); (11) *Thermococcus gorgonarius* (40-54% G+C); (12) *Thermococcus pacificus* (40-54% G+C); (13) *Thermococcus zilligii* (40-54% G+C); (14) *Haloferax volcanii* WR341 (66% G+C); (15) *Haloferax volcanii* WR586 (66% G+C).
Figure 9:
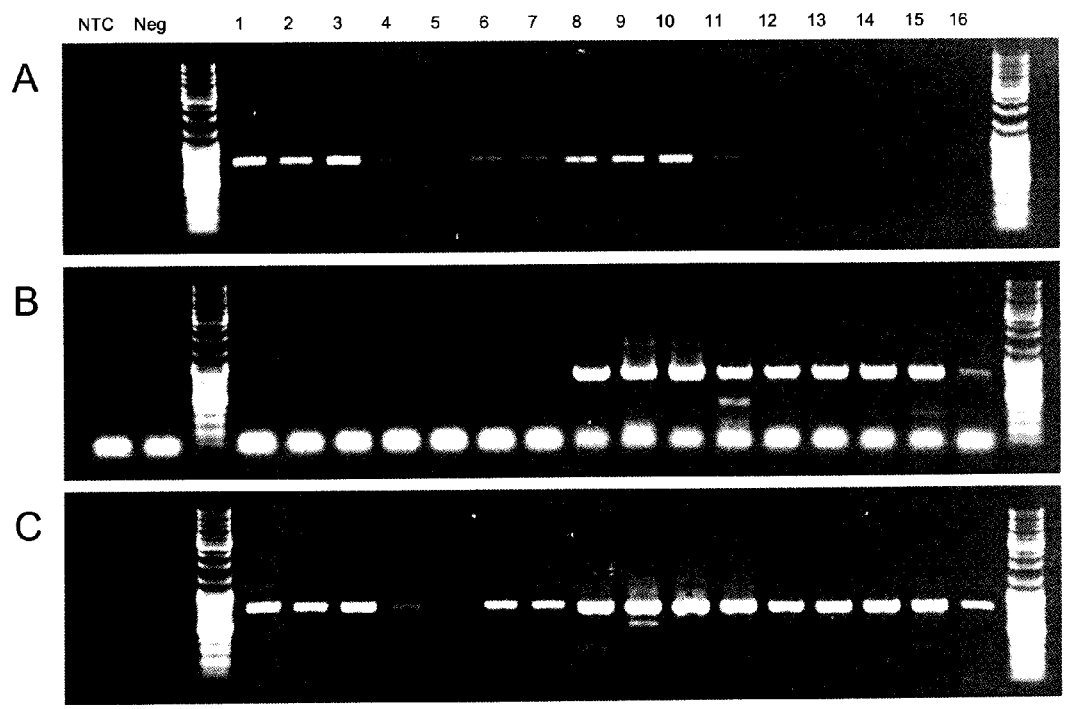

In an embodiment, the archaea organisms detected, identified and/or quantified is listed in Table 2 and/or FIG. 2 and/or FIG. 9. The sequences of the thermosome genes, amplifiable by the primers described herein (e.g. approx 760 nucleotides amplifiable by SEQ ID NO:3, 4, 5 and/or 6), are herein incorporated by reference.

Another aspect of the disclosure includes a kit for the detection of an archaea thermosome polynucleotide comprising:
  a) a polynucleotide comprising at least 10 contiguous nucleotides of: SEQ ID NO:1, SEQ ID NO:2, GGI CCI MRR GGI ITI GAY AAR ATG (SEQ ID NO:3), GCI AII TCR TCI ATI CCY TTY TG (SEQ ID NO:4), GGC CCG MG GGC ATG GAC MG ATG (SEQ ID NO:5) or GCC ATG TCG TCG ATG CCC TTC TG (SEQ ID NO:6); and/or
  b) a polynucleotide having at least 80% sequence identity to: SEQ ID NO:1, SEQ ID NO:2, GGI CCI MRR GGI ITI GAY AAR ATG (SEQ ID NO:3), GCI AII TCR TCI ATI CCY TTY TG (SEQ ID NO:4), GGC CCG MG GGC ATG GAC MG ATG (SEQ ID NO:5) or GCC ATG TCG TCG ATG CCC TTC TG (SEQ ID NO:6); or
  c) a polynucleotide which is complementary or reverse complementary to a) and/or b).

In an embodiment, the kit for the detection of an archaea thermosome polynucleotide comprises an isolated nucleic acid molecule or primer described herein wherein the isolated nucleic acid molecule and/or primer corresponds to a portion of an archaea thermosome gene which is diagnostic for the presence of archaea.

In another aspect, the disclosure includes a kit for detecting the presence of an archaea comprising a primer set described herein wherein the set corresponds to a portion of an archaea thermosome gene which is diagnostic for the presence of archaea.

In another embodiment, the disclosure includes a kit for the detecting the presence of an archaea organism comprising a primer pair, wherein the pair is capable of priming a nucleic acid amplification reaction that amplifies a region of nucleic acid within the archaea thermosome gene which is diagnostic for the presence of archaea.

In an embodiment, the primer set comprises one or more upstream primers each comprising a polynucleotide consisting of: SEQ ID NO: 1, GGI CCI MRR GGI ITI GAY AAR ATG (SEQ ID NO:3) or GGC CCG MG GGC ATG GAC MG ATG (SEQ ID NO:5), and one or more downstream primers, each comprising a polynucleotide consisting of: SEQ ID NO:2, GCI AII TCR TCI ATI CCY TTY TG (SEQ ID NO:4) or GCC ATG TCG TCG ATG CCC TTC TG (SEQ ID NO:6).

In another embodiment, the primer set a first primer pair comprising: a polynucleotide consisting of GGI CCI MRR GGI ITI GAY AAR ATG (SEQ ID NO:3) and a polynucleotide consisting of GCI AII TCR TCI ATI CCY TTY TG (SEQ ID NO:4), and a second primer pair comprising: a polynucleotide consisting of GGC CCG AAG GGC ATG GAC AAG ATG (SEQ ID NO:5) and a polynucleotide consisting of GCC ATG TCG TCG ATG CCC TTC TG (SEQ ID NO:6), wherein the ratio of the first primer pair to the second primer pair is about 1:1.

In yet another embodiment, the primer set comprises: a first primer pair comprising: a polynucleotide consisting of GGI CCI MRR GGI ITI GAY AAR ATG (SEQ ID NO:3) and a polynucleotide consisting of GCI AII TCR TCI ATI CCY TTY TG (SEQ ID NO:4), and a second primer pair comprising: a polynucleotide consisting of GGC CCG AAG GGC ATG GAC AAG ATG (SEQ ID NO:5) and a polynucleotide consisting of GCC ATG TCG TCG ATG CCC TTC TG (SEQ ID NO:6), wherein the ratio of the first primer pair to the second primer pair is about 3:1.

In another embodiment, the kit further comprises optionally
a) one or more of internal standard/positive control DNA template,
b) PCR reagents (such as thermostable DNA polymerase, deoxynucleotides, amplification primers for control DNA, buffers etc) and/or
c) instructions for use.

The kit can optionally comprise sample collection tubes, a thermostable polymerase, a mixture of four different deoxynucleotide triphosphates, a nucleic acid-binding fluorescent molecule, at least one pair of internal sample control primers, at least one internal template control and at least one pair of internal template control primers, and a control DNA template comprising a complementary sequence to a portion of at least one region of nucleic acid within the thermosome archaea gene which is capable of being amplified with the at least one pair of archaea diagnostic primer sequences.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be closed ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. For example, an isolated nucleic acid molecule, probe or primer can include more than one, including for example a mixture.

The term "about" means plus or minus 0.1 to 50%, 5-50%, or 10-40%, 10-20%, 10%-15%, preferably 5-10%, most preferably about 5% of the number to which reference is being made.

Further, the definitions and embodiments described are intended to be applicable to other embodiments herein described for which they are suitable as would be understood by a person skilled in the art. For example, in the above passages, different aspects are defined in more detail. Each aspect so defined can be combined with any other aspect or aspects unless clearly indicated to the contrary. In particular, any feature indicated as being preferred or advantageous can be combined with any other feature or features indicated as being preferred or advantageous.

The following non-limiting examples are illustrative of the present disclosure:

EXAMPLES

Example 1

Methods

Primer design was based on type II chaperonin DNA sequences collected from NCBI GenBank. When multiple copies of the thermosome gene were present in an archaeal genome, all the identified copies were included in the analysis. Simultaneously, the 16S rRNA gene sequence from the corresponding strain were also collected and used for phylogenetic comparison. Sequences were aligned used ClustaiX software (27) and visualized using GeneDoc. Phylooenetic, analysis was performed using Phylip software.

Archaeal DNA used for initial testing was graciously donated by Ken Jarrell (Queen's University), Charles Greer (NCR-BRI), Odille Tresse (NRC-BRI), Allison Murray (Desert Research Institute, Reno, Nev.) and Sean Hemmingsen (NCR-PBI). Various PCR conditions were tried and optimized to a standard protocol consisting of 1×PCR buffer (Invitrogen), 2.5 mM $MgCl_2$, 400 nM of each primer, 200 µM dNTPs and 2.5 U of Platinum Taq polymerase (Invitrogen) per 50 µl reaction. PCR primers used are listed in Table 1. PCR reactions were carried out at 94° C. for 3 min, 40 cycles of 94° C. for 30 sec, 46-57° C. gradient for 1 min, 72° C. for 1 min, followed by 72° C. for 10 min. PCR products were visualized on 1% agarose gels as per standard procedures.

Results

Figure 1A:
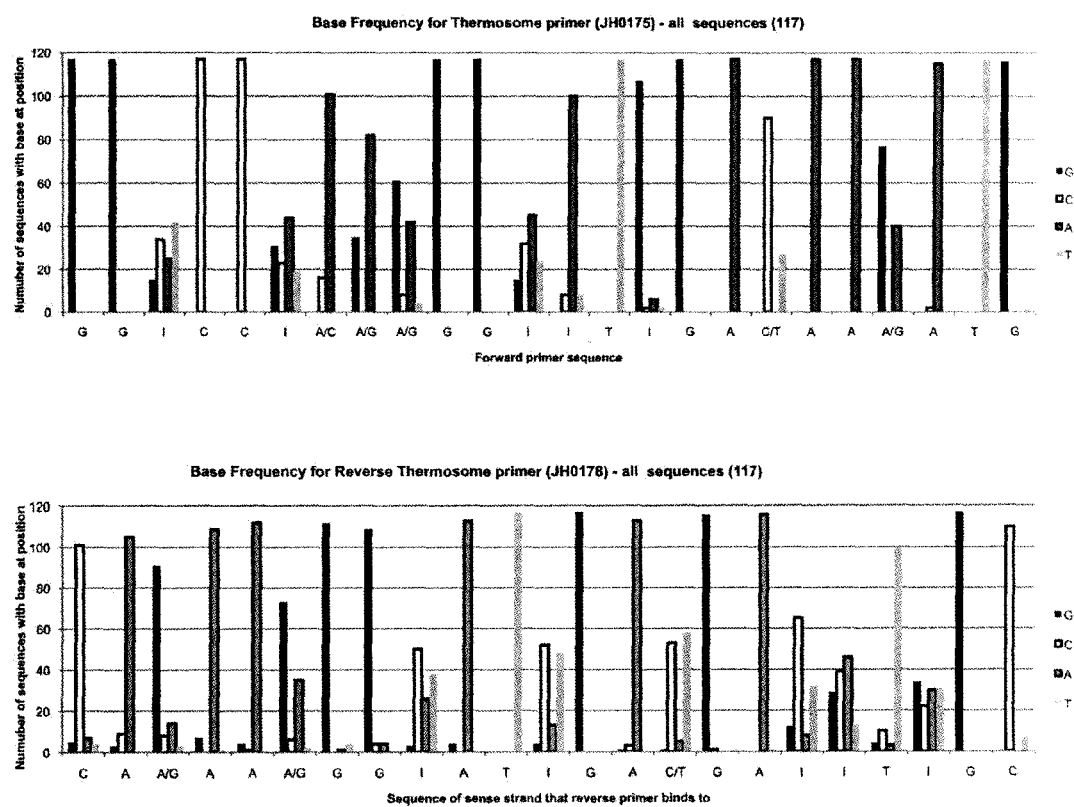
FIG. 1. Base frequency analysis of JH0175 and JH0178 (SEQ ID NO:3 and 4) and JH0268 and JH0269 (SEQ ID NO: 5 and 6) indicating the frequency of each nucleotide at each position in the multiple sequence alignment of 117 archaeal thermosome genes. The DNA sequence listed at the bottom represents the primer sequence (forward primer, upper panel) or the primer landing site (reverse primer, lower panel). "I" represents inosine, a nucleotide analog with the property of base pairing with any nucleotide. Inosine residues are included to reduce primer degeneracy created by accommodating highly variable positions (e.g. where all 4 nucleotides occur with equal or nearly equal frequency).
Figure 1B:
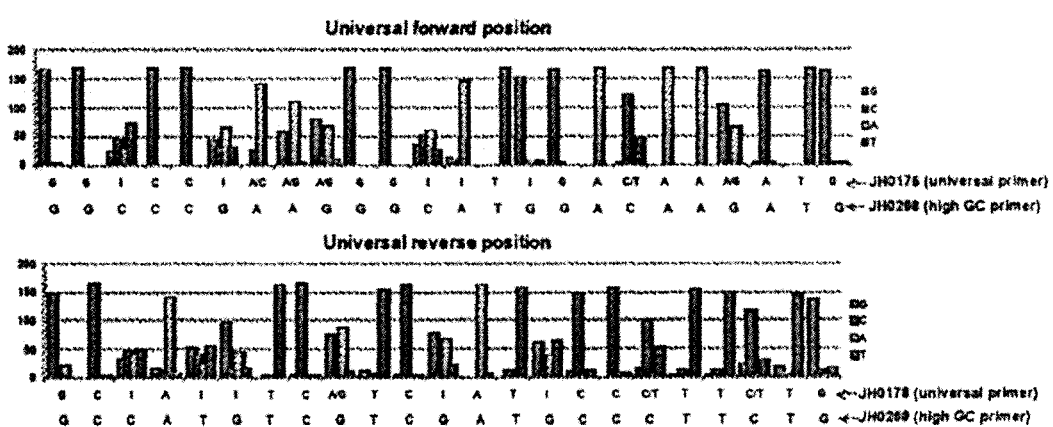

JH0175/JH178 primer design. Multiple sequence alignments were made of all the available thermosome gene sequences from archaea (117 sequences). Conserved regions were identified and base frequency analysis was performed to determine if universal primers could be designed. A forward and reverse region was chosen based on an acceptable region of DNA conservation (FIG. 1). This primer set was designated JH0175/JH0178 (sequences in Table 1).

Figure 3:
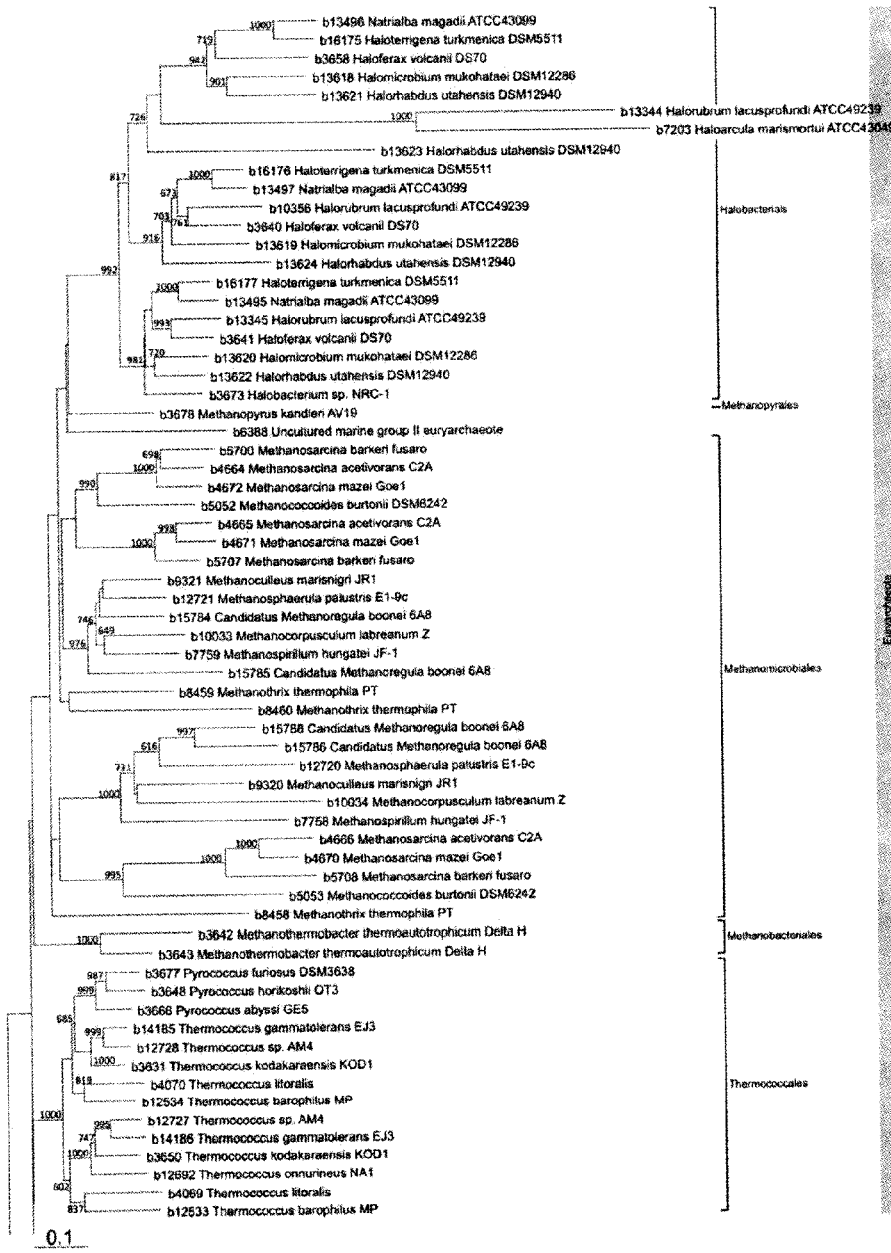
FIG. 3. Phylogenetic tree of archaeal species based on an alignment of the ~760 bp region of the chaperonin (thermosome) gene amplified by universal primers JH0175/JH0178 (SEQ ID NO:3/SEQ ID NO:4).

Evaluation of the thermosome gene target as a phylogenetically informative region. Once a universal PCR primer set was chosen, the proposed universal target (UT) region (~760 bp in length) was evaluated to determine if the sequence region would generate phylogenetically useful data. The proposed UT region from all thermosome sequences was generated in silico and phylogenetic trees were constructed based on the DNA sequence data. These trees were compared to 16S rRNA-based phylogenetic trees (from the same strain) to ascertain whether the same family branching structure was generated and whether greater phylogenetic resolution was obtainable at the genus/species level (visualized by longer branch lengths). These trees are shown in FIGS. 2 and 3. Note that different strains of *Methanococcus mariplaudis* in the thermosome UT tree are resolvable, but these strains are identical in 16S rRNA sequence.

Testing with purified archaeal DNA. To begin evaluating the JH0175/JH0178 thermosome primer set, purified archaeal DNA was obtained and used as PCR template material. Well-established PCR primer sets that target the 16S rRNA gene (DeLong and Baker sets) and mcrA gene (a methanogenesis-specific enzyme; Mihajlovski set) were tested in parallel to evaluate performance. Table 2 summarizes the testing results. PCR results indicated that the thermosome primer set worked as well or better that the preexisting universal archaeal primer sets, with the exception of the high GC organisms (Halophile group; GC content ~68%)

Figure 4:
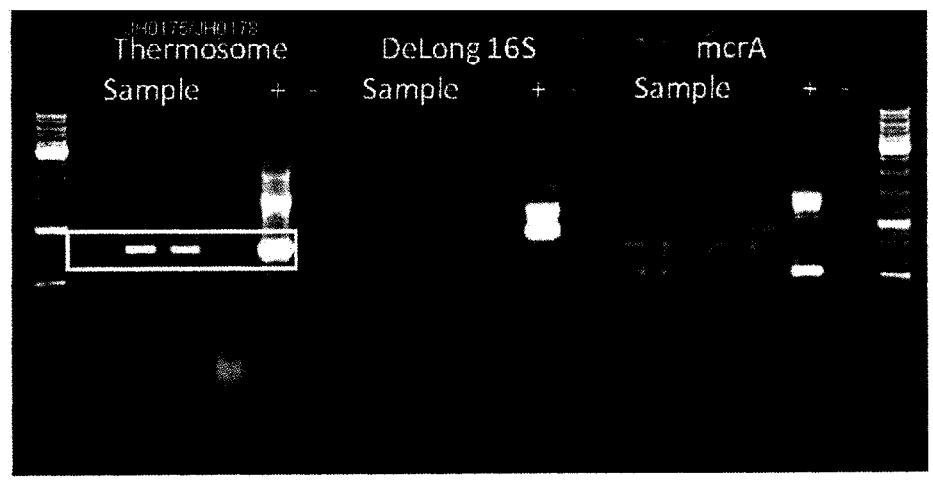
FIG. 4. PCR results showing the primer performance with rumen contents as the DNA template. Note the clear positive bands with the thermosome primers that were not reproducible with the other primer sets. (+=positive control template DNA, −=no DNA negative control). White box encloses the JH0175/JH0178 (SEQ ID NO:3/SEQ ID NO:4) PCR product.

Application of universal thermosome primers to complex samples (rumen contents). To determine the performance of the JH0175/JH0178 primer set with a complex template, rumen samples from dairy cows at the University of Saskatchewan dairy barn were obtained and total DNA was extracted using a standard mechanical shearing/phenol:chloroform procedure. Amplification was carried out and PCR products visualized on a gel. FIG. 4 shows the performance of the thermosome primer set to be superior to the 16S rRNA and mcrA primer sets.

Based on the computational analysis of the thermosome UT region generated by the JH0175/JH0178 primer set and the performance of these primers under laboratory conditions, there is sufficient evidence to consider this primer set useful for the universal detection and identification of archaea. The technology could be applied in any field where Archaea play an important biological role. This includes animal nutrition and intestinal health in ruminants (cattle, goats, sheep, bison or deer) and management of waste from ruminants (where archaeal species are responsible for greenhouse gas emissions). An additional application would be in the characterization of microbial consortia with biotechnological applications, for research, regulatory or marketing purposes.

Archaea are ubiquitous in the environment and their roles in fundamental biological processes are only beginning to be understood. They are also common inhabitants of the mammalian gastrointestinal tract and are thought to play a significant ecological role in this complex community.

Example 2

The primer set JH0175 and JH0178 have been tested and it has been found that these primers could amplify the target gene from all archaeal species tested, to a maximum guanine plus cytosine (G+C) content of about 54%.

Figure 5:
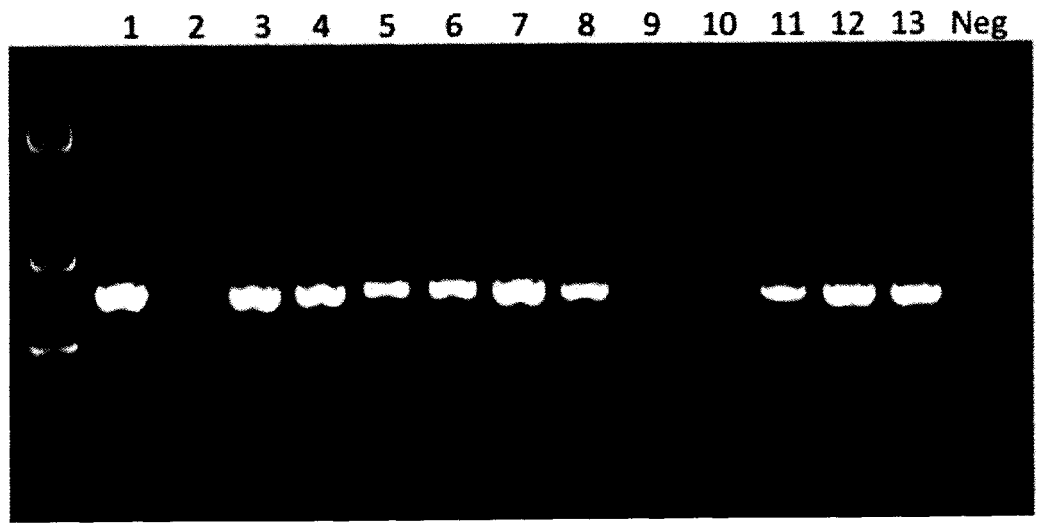
FIG. 5. PCR products from the JH0175/JH0178 (SEQ ID NO:3/SEQ ID NO:4) primer set using purified genomic DNA from archaeal isolates as templates. Lanes indicate (1) *Methanococcus voltae* (27% GC); (2) *Halobacterium salinarum* (formerly *Halobacterium halobium*) (66% GC); (3) *Methanococcus vannielii* (31% GC); (4) *Methanococcus maripaludis* (33%); (5) *Methanotorris igneus* (38% GC); (6) *Sulfolobus solfataricus* (36% GC); (7) *Sulfolobus* sp. (33-36% GC); (8) *Thermoplasma acidophilum* (46% GC); (9) *Halobacterium salinarum* ATCC33170 (66% GC); (10) *Halobacterium salinarum* ATCC33171 (66% GC); (11) *Thermococcus gorgonarius* (40-54% GC); (12) *Thermococcus pacificus* (40-54% GC); (13) *Thermococcus zilligii* (40-54% GC); (Neg) PCR no template control.

PCR products from the JH0175/JH0178 primer set using purified genomic DNA from archaeal isolates as templates are shown in FIG. 5. Lanes indicate (1) *Methanococcus voltae* (27% GC); (2) *Halobacterium salinarum* (formerly *Halobacterium halobium*) (66% GC); (3) *Methanococcus vannielii* (31% GC); (4) *Methanococcus maripaludis* (33%); (5) *Methanotorris igneus* (38% GC); (6) *Sulfolobus solfataricus* (36% GC); (7) *Sulfolobus* sp. (33-36% GC); (8) *Thermoplasma acidophilum* (46% GC); (9) *Halobacterium salinarum* ATCC33170 (66% GC); (10) *Halobacterium safinarum* ATCC33171 (66% GC); (11) *Thermococcus gorgonarius* (40-54% GC); (12) *Thermococcus pacificus* (40-54% GC); (13) *Thermococcus zilligii* (40-54% GC); (Neg) PCR no template control.

Example 3

To overcome the problem of no amplification with high G+C content templates, an additional set of PCR primers targeting the highest G+C organism were designed, *Halobacterium salinarum* (66% G+C) (Accession Number: AE005099). These primers were designated JH0268 and JH0269 and anneal to the same sites targeted by the original primers (FIG. 1B; 6; Table 3).

Figures 6, 7:
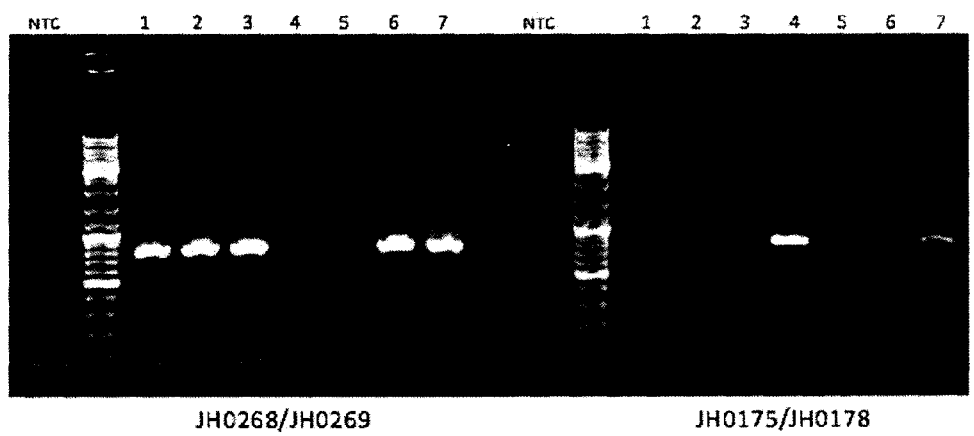
FIG. 6. The JH0268/JH0269 (SEQ ID NO:5/SEQ ID NO:6) primers are versions of the JH0175/JH0178 (SEQ ID NO:3/SEQ ID NO:4) pair where any degenerate position in the original (I, M, R, Y) has been replaced by the specific nucleotide base found in the high G+C organisms.
FIG. 7. PCR products from either the JH0268/JH0269 (SEQ5/SEQ6) or JH0175/JH0178 (SEQ ID NO:3/SEQ ID NO:4) primer set using purified genomic DNA from archaeal isolates as templates. Lanes indicate (NTC) PCR no template control; (1) *Halobacterium salinarum* (formerly *Halobacterium halobium*) (66% G+C); (2) *Halobacterium salinarum* ATCC33170 (66% G+C); (3) *Halobacterium salinarum* ATCC33171 (66% G+C); (4) *Methanococcus maripaludis* (33% G+C); (5) *Sulfolobus* sp. (33-36% G+C); (6) *Thermoplasma acidophilum* (46% G+C); (7) *Thermococcus gorgonarius* (40-54% G+C).

The JH0268/JH0269 primers are versions of the JH0175/JH0178 pair where any degenerate position in the original (I, M, R, Y) has been replaced by the specific nucleotide base found in the high G+C organisms (FIG. 6). When these primers were tested, they amplified not only the *Halobacterium salinarum* sequences, but also other high and mid-range G+C archaea (including *Haloferax volcanii* (Accession Numbers: AF010469, AF010470, AF298660), *Thermoplasma acidophilum* (Accession Numbers: NC_002578, NC_002578) and *Thermococcus gorgonarius*)

When tested individually, the original JH0175/JH0178 primer set amplified targets from representative genomes with G+C contents of 27-~66%. Conversely, the JH0268/JH0269 primer set reliably amplified targets from representative genomes with G+C contents of ~40-66% (FIG. 7).

Figure 8:
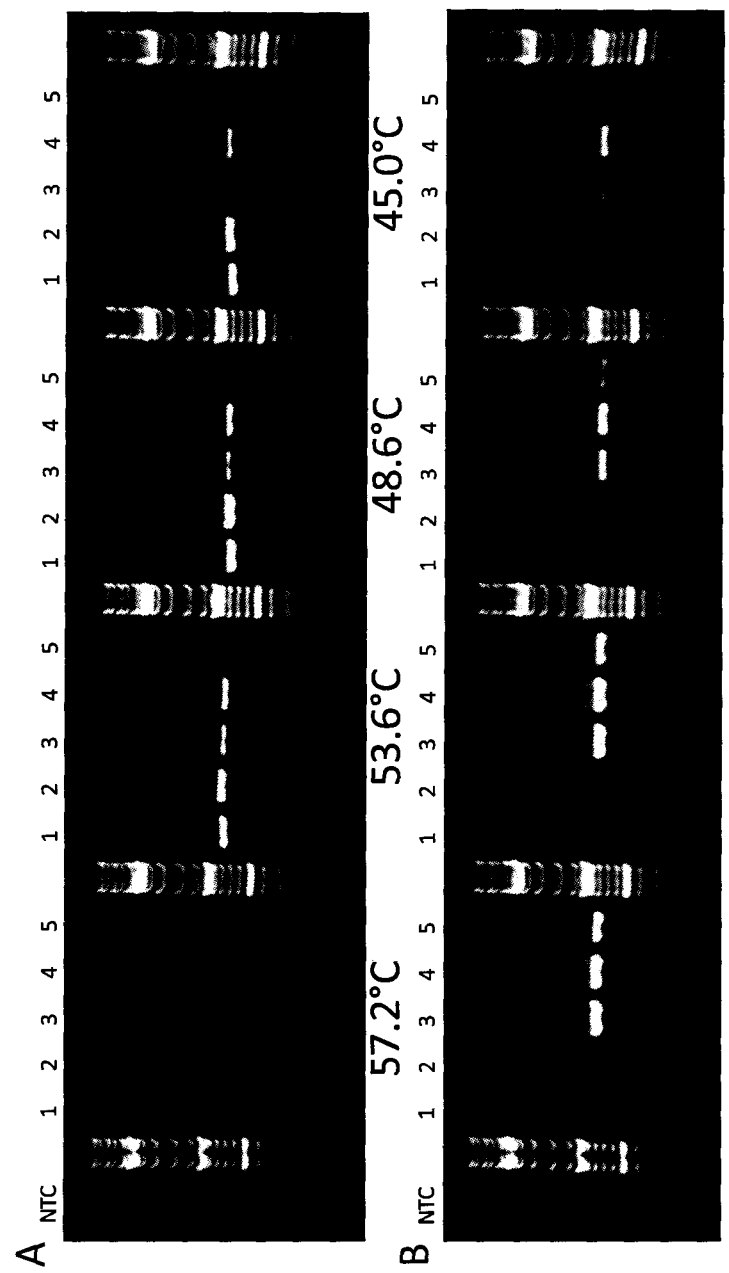
FIG. 8. PCR products from an annealing temperature gradient PCR reaction with (A) JH0175/JH0178 (SEQ ID NO:3/SEQ ID NO:4) or (B) JH0268/JH0269 (SEQ ID NO:5/SEQ ID NO:6) primer sets using purified genomic DNA from archaeal isolates as templates. Lanes indicate (NTC) PCR no template control; (1) *Methanococcus maripaludis* (33% G+C); (2) *Sulfolobus* sp. (33-36% G+C); (3) *Thermoplasma acidophilum* (46% G+C); (4) *Thermococcus gorgonarius* (40-54% G+C); (5) *Haloferax volcanii* (66% G+C). The annealing temperature used for each reaction is indicated between the panels.

Based on the temperature gradient information demonstrated in FIG. 8, the following PCR amplification program was designed:
98° C. for 3 min, followed by 40 cycles of amplification with 98° C. for 30 sec, 54° C. for 30 sec and 72° C. for 1 min, followed by 72° C. for 10 min and a 10° C. final hold temperature.

Presently, different cocktails of the primer sets, JH0175/JH0178:JH0268/JH0269, are being tested to against the range of archaeal genomic DNAs to determine what mixture can successfully generate an amplicon from every G+C content range.

Successful amplification obtained with testing archaea from a culture collection comprising from 27% to 66% G+C content indicates that this improved PCR protocol will allow for the successful amplification of any archaeal thermosome sequence from an unknown sample, regardless of the archaeal species present (and their G+C content) (FIG. 9).

The new primer set (JH0268/JH0269) can also be used on its own for the amplification of partial thermosome sequence from known high G+C templates (e.g. from isolated archaea).

Example 4

Amplification using primer sets SEQ ID NO:3/SEQ ID NO:4: SEQ ID NO:5/SEQ ID NO:6 at a ratio of 1:7, 1:3, 1:1, 3:1, 7:1, 15:1, 31:1, 63:1, 127:1 and 255:1 were tested. All primer sets produced detectable product.

The optimal ratio of primer pair mixing was 7:1, with the degenerate primer pair (SEQ ID NO:3 and SEQ ID NO:4) being present at 7 parts to the specific primer pair (SEQ ID NO:5 and SEQ ID NO:6) being present at 1 part (FIG. 9B). This may be because, although the degenerate primer pair includes the specific primer sequence, a small proportion of specific primer targeting high G+C organisms improved the overall efficiency of the high G+C amplifications without inhibiting the low G+C amplifications.

It was found that the most universal amplification of archaea of different G+C contents, was obtained using the primers with a 7:1 ratio. For targeting high G+C organism, it was found that 1:7 to 7:1 gave good amplification. For targeting low G+C organisms, 7:1 to 255:1 gave good amplification. The 7:1 ratio is the overlap where all G+C organisms appear to amplify well.

Example 5

A Universal PCR Target/System for Archaea

The prokaryotic, world is divided into the Bacteria and Archaea domains. Although these two groups are evolutionarily and biochemically distinct, both are found in almost every environment investigated. Within the bacterial realm, robust universal PCR primer sets have been well-characterized and utilized to target the bacterial 16S rRNA gene and the croup I chaperonin (cpn60) gene. Both have provided a wealth of data towards understanding the bacterial members of complex communities, with the protein-coding chaperonin gene having advantages in terms of phylogenetic resolution (the ability to distinguish closely related species or strains). Alternatively, within the archaeal realm, universal PCR primers for the entire domain have remained limited to the archaeal 16S rRNA gene. To determine if a universally-conserved archaeal protein-encoding gene could reproduce the phylogeny of the archaeal 16S rRNA gene and improve upon individual strain resolution, we choose to evaluate the group II archaeal chaperonin genes (known as the thermosome, TF55, CCT or TCP -1) as a potential archaeal marker. One immediate advantage to targeting the archaeal thermosome as an identifying genetic marker is that a curated database of group II chaperonin gene sequences is already being maintained as part of the publicly-available bacterial chaperonin database (cpnDB), meaning that the infrastructure necessary to translate this target into a practical research tool is already in place.

Group II Chaperonin Sequences are Phylogenetically Informative

Given that most archaea possess 2-3 distinct group II chaperonin subunits (alpha, beta and gamma), 166 full-length chaperonin sequences were compiled from 84 sequenced archaeal genomes and group II chaperonin phylogenes were compared to 16S rRNA gene phylogenes from matched genomes. Both the full length chaperonin phylogeny and the proposed universal target sequence create comparable phylogenes. Note the difference in scale of the branch lengths, indicating the finer resolution of the chaperonin tree (FIG. 10).

Universal PCR Primers to Detect all Archaeal Group II Chaperonins are

Both DNA and protein sequence alignments were assembled for all 166 group II chaperonin genes (included alpha, beta and gamma subunits). Regions of conservation were identified and degenerate primers JH0175 (forward) and JH0178 (reverse) were created. These primers amplify an ~750 bp product (+/−25 bp, depending on species) that was designated the universal target. After initial testing, it was determined that a specific version of universal primers targeting high GC content organisms, JH0268 (forward) and JH0269 (reverse), improved target amplification across the domain.

The frequency of nucleotides at each position and the sequence of the primer pairs is provided in FIG. 1.

The universal degenerate JH0175/JH0178 primer set, the high GC organism JH0268/JH0269 primer set and a cocktail of 7:1 JH0175/JH0178:JH0268/JH0269 was tested with purified genomic DNA (1.0 ng/reaction) from 16 archaeal isolates. The universal primer set amplified group II chaperonin sequences from 28-54% GC content genomes, while the high GC primer set amplified sequences from 46-66% GC content genomes. When all four primers were mixed at a ratio of 7:1 universal set: high GC set, all archaeal templates generated group II chaperonin PCR product (FIG. 9).

The Group II Chaperonin Primers Compared to 16S rRNA Primers or Methanogen-Specific (mcrA) Primers in Field Samples—Rumen Contents from Dairy Cows on 2 Different Diets Group II Chaperonin Identification Agreed with Other Methods and Had Finer Strain Resolution To evaluate the group II chaperonin primers in a field sample, rumen contents were collected from 6 dairy cows; 4 on a regular dairy cow diet and 2 on a dry food diet. Total DNA was extracted from each sample and PCR was performed using either the universal group II chaperonin (tcp) primers (JH0175/JH0178), universal 16S rRNA gene primers (1) or methanogen-specific methyl-coenzyme M reductase gene, mcrA, primers (25). Products from cows on the same diet were pooled and clone libraries were made for each primer/diet combination. In addition, PCR product from tcp primers/dry food diet were included in a pyrosequencing run.

Species identified as a nearest neighbour for sequences detected in rumen samples by diet and target gene.

| Nearest Neighbour | Regular diet | | | Dry food diet | | | | Total |
|---|---|---|---|---|---|---|---|---|
| | tcp lib[1] | 16S lib[2] | mcrA lib[3] | tcp lib | 16S lib | mcrA lib | tcp pyro[4] | |
| Methanobrevibacter smithii | 24[5] | 37 | 21 | 39 | 52 | 26 | 276 | 475 |
| Methanobrevibacter ruminantium | 11 | 28 | 45 | 12 | 9 | 23 | 146 | 274 |
| Methanosphaera stadtmanae | 17 | 1 | 8 | 8 | 4 | 16 | 88 | 142 |
| Methanosphaerula palustris | 0 | 0 | 0 | 0 | 6 | 0 | 4 | 10 |
| Methanocorpusculum labreanum | 0 | 0 | 0 | 0 | 0 | 12 | 1 | 13 |
| Methanothermobacter thermoautotrophicus | 0 | 0 | 0 | 0 | 0 | 0 | 3 | 3 |
| Methanococcus maripaludis | 0 | 0 | 0 | 0 | 0 | 1 | 0 | 1 |
| Methanoculleus marisnigri | 0 | 0 | 1 | 0 | 0 | 0 | 0 | 1 |
| Methanococcoides burtonii | 0 | 0 | 1 | 0 | 0 | 0 | 0 | 1 |
| Methanosarcina acetivorans | 0 | 0 | 0 | 0 | 0 | 0 | 1 | 1 |
| Staphylothermus hellenicus | 0 | 0 | 0 | 0 | 0 | 0 | 3 | 3 |
| Total sequences | 52 | 66 | 76 | 59 | 71 | 78 | 522 | 924 |

[1]Thermosome gene target, clone library results
[2]16S rRNA gene target, clone library results
[3]Methyl co-enzyme M reductase gene target, clone library results
[4]Thermosome gene target, pyrosequencing results
[5]Number of sequence reads Comparison of *Methanobrevibacter smithii* Sequences Obtained from 16S, tcp and mcrA Clone Libraries Neighbour-joined phylogenetic trees of sequences identified as *Methanobrevibacter smithii* were generated to evaluate the strain resolution of each target (FIG. 11). Numbers in parentheses indicate times when the same sequences were detected more than once in the dataset. *Methanococcus maripaludis* was included as an outlier. Note the different length of the scale bar between trees.

Conclusion

Group II chaperonin universal PCR can give robust detection of archaeal species while generating finer strain resolution than 16S rRNA gene targets.

Example 6

In some situations a single primer pair (or a skewed ratio) may be preferable. For example, looking at the rumen of cattle (source of greenhouse gas), low G+C archaea are expected.

It was found that using primer pair comprising SEQ ID NO:3/SEQ ID NO:4 sequences amplified cattle rumen archaea organisms.

Where high G+C organisms are expected such as in run-off from a mining site, primers comprising sequences such as SEQ ID NO:5/SEQ ID NO:6 sequences (or a ratio skewed to them) would be expected to be useful.

Example 7

It has been found using primer pair consisting of SEQ ID NO.3/SEQ ID NO.4 that archaea sequences from anaerobic digestors can be amplified. Profiles of productive archaea communities that enhance biogas production in anaerobic digestors can be determined and used to modify unproductive digestors to produce more biogas.

Example 8

As it is known that archaea (specifically methanogens) can use hydrocarbons as an energy source and can grow in oil and gas pipelines, and as this growth causes the organisms to release hydrogen sulfide and "sour" lines, the primer pairs disclosed herein can be used to identify these organisms to reduce or monitor pipeline souring and corrosion.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

1. Baker, G. C., J. J. Smith, and D. A. Cowan. 2003. Review and re-analysis of domain-specific 16S primers. J Microbiol Methods 55:541-55.
2. Brousseau, R., J. E. Hill, G. Prefontaine, S. H. Goh, J. Harel, and S. M. Hemmingsen. 2001. Streptococcus suis serotypes characterized by analysis of chaperonin 60 gene sequences. Applied and Environmental Microbiology 67:4828-33.
3. Chaban, B., K. M. Musil, C. G. Himsworth, and J. E. Hill. 2009. Development of cpn60-based real-time quantitative PCR assays for the detection of 14 *Campylobacter* species and application to screening canine fecal samples. Applied and Environmental Microbiology 75:3055-3061.
4. Coetser, S. E., and T. E. Cloete. 2005. Biofouling and biocorrosion in industrial water systems. Crit Rev Microbiol 31:213-32.
5. DeLong, E. F. 1992. Archaea in coastal marine environments. Proc Natl Acad Sci USA 89:5685-9.
6. Desai, A. R., K. M. Musil, A. P. Carr, and J. E. Hill. 2009. Characterization and quantification of feline fecal microbiota using cpn60 sequence-based methods and investigation of animal-to-animal variation in microbial population structure. Vet Microbiol 137:120-128.
7. Dumonceaux, T. J., J. E. Hill, S. A. Briggs, K. K. Amoako, S. M. Hemmingsen, and A. G. Van Kessel. 2006. Enumeration of specific bacterial populations in complex intestinal communities using quantitative PCR based on the chaperonin-60 target. Journal of Microbiological Methods 64:46-62.
8. Dumonceaux, T. J., J. E. Hill, S. M. Hemmingsen, and A. G. Van Kessel. 2006. Characterization of intestinal microbiota and response to dietary virginiamycin supplementation in the broiler chicken. Applied and Environmental Microbiology 72:2815-2823.
9. Dumonceaux, T. J., J. E. Hill, C. Pelletier, M. G. Paice, A. G. Van Kessel, and S. M. Hemmingsen. 2006. Molecular characterization of microbial communities in Canadian pulp and paper activated sludge and quantification of a novel *Thiothrix eikelboomii*-like bulking filament. Canadian Journal of Microbiology 52:494-500.
10. Dumonceaux, T. J., J. Schellenberg, V. Goleski, J. E. Hill, W. Jaoko, J. Kimani, D. Money, T. B. Ball, F. A. Plummer, and A. Severini. 2009. Multiplex detection of bacteria associated with normal microbiota and with bacterial vaginosis in vaginal swabs using oligonucleotide-coupled fluorescent microspheres. Journal of Clinical Microbiology 47:4067-4077.
11. Goh, S. H., A. W. Chow, and S. M. Hemmingsen. 1998. HSP-60 genomic locus and primers for species identification. U.S. Pat. No. 5,708,160.
12. Goh, S. H., A. W. Chow, and S. M. Hemmingsen. 1999. Universal targets for species identification. U.S. Pat. No. 5,989,821.
13. Goh, S. H., R. R. Facklam, M. Chang, J. E. Hill, G. J. Tyrrell, E. C. Burns, D. Chan, C. He, T. Rahim, C. Shaw, and S. M. Hemmingsen. 2000. Identification of *Enterococcus* species and phenotypically similar *Lactococcus* and *Vagococcus* species by reverse checkerboard hybridization to chaperonin 60 gene sequences. Journal of Clinical Microbiology 38:3953-9.
14. Haigh, J. C., V. Gerwing, J. Erdenebaatar, and J. E. Hill. 2008. A novel clinical syndrome and detection of *Anaplasma ovis* in Mongolian reindeer (*Rangifer tarandus*). Journal of Wildlife Diseases 44:569-77.
15. Hill, J. E., S. H. Goh, D. M. Money, M. Doyle, A. Li, W. L. Crosby, M. Links, A. Leung, D. Chan, and S. M. Hemmingsen. 2005. Characterization of vaginal microflora of healthy, nonpregnant women by chaperonin-60 sequence-based methods. American Journal of Obstetrics and Gynecology 193:682-92.
16. Hill, J. E., S. M. Hemmingsen, B. G. Goldade, T. J. Dumonceaux, J. Klassen, R. T. Zijlstra, S. H. Goh, and A. G. Van Kessel. 2005. Comparison of ileum microflora of pigs fed corn-, wheat-, or barley-based diets by chaperonin-60 sequencing and quantitative PCR. Applied and Environmental Microbiology 71:867-75.

17. Hill, J. E., S. M. Hemmingsen, and J. R. Town. 2009. Strong PCR primers and primer cocktails. U.S. Pat. No. 7,507,535.
18. Hill, J. E., R. P. Seipp, M. Betts, L. Hawkins, A. G. Van Kessel, W. L. Crosby, and S. M. Hemmingsen. 2002. Extensive profiling of a complex microbial community by high-throughput sequencing. Appl Environ Microbiol 68:3055-66.
19. Hill, J. E., R. P. Seipp, M. Betts, L. Hawkins, A. G. Van Kessel, W. L. Crosby, and S. M. Hemmingsen. 2002. Extensive profiling of a complex microbial community by high-throughput sequencing. Applied and Environmental Microbiology 68:3055-66.
20. Hill, J. E., J. R. Town, and S. M. Hemmingsen. 2006. Improved template representation in cpn60 PCR product libraries generated from complex templates by application of a specific mixture of PCR primers. Environmental Microbiology 8:741-746.
21. Large, A. T., and P. A. Lund. 2009. Archaeal chaperonins. Front Biosci 14:1304-24.
22. Lazarovits, G., P. Abbasi, K. Conn, J. E. Hill, and S. M. Hemmingsen. 2009. Fish emulsion and liquid swine manure: model systems for development of organic amendments as fertilizers with disease suppressive properties, p. 49-68. In W. Bettiol and M. A. B. Morandi (ed.), Biocontrole de Doencas de Plantas: Uso e Perspectivas. Embrapa, Sao Paolo.
23. Leahy, S. C., W. J. Kelly, E. Alternann, R. S. Ronimus, C. J. Yeoman, D. M. Pacheco, D. Li, Z. Kong, S. McTavish, C. Sang, S. C. Lambie, P. H. Janssen, D. Dey, and G. T. Attwood. The genome sequence of the rumen methanogen *Methanobrevibacter ruminantium* reveals new possibilities for controlling ruminant methane emissions. PLoS One 5:e8926.
24. Masson, L., C. Maynard, R. Brousseau, S. H. Goh, S. M. Hemmingsen, J. E. Hill, A. Paccagnella, R. Oda, and N. Kimura. 2006. Identification of pathogenic Helicobacter species by chaperonin-60 differentiation on plastic DNA arrays. Genomics 87:104-12.
25. Mihajlovski, A., M. Alric, and J. F. Brugere. 2008. A putative new order of methanogenic Archaea inhabiting the human gut, as revealed by molecular analyses of the mcrA gene. Res Microbiol 159:516-21.
26. Schellenberg, J., M. G. Links, J. E. Hill, T. J. Dumonceaux, G. A. Peters, S. Tyler, B. Ball, A. Severini, and F. A. Plummer. 2009. Pyrosequencing of the chaperonin-60 universal target for phylogenetic analysis of microbial communities. Applied and Environmental Microbiology 75:2889-2898.
27. Thompson, J. D., T. J. Gibson, and D. G. Higgins. 2002. Multiple sequence alignment using ClustalW and ClustalX. Curr Protoc Bioinformatics Chapter 2:Unit 2 3.
28. Vermette, C. J., A. H. Russell, A. R. Desai, and J. E. Hill. 2009. Resolution of phenotypically distinct strains of *Enterococcus* spp. in a complex microbial community using cpn60 universal target sequencing. Microbial Ecology [Epub ahead of print]:doi:10.1007/s00248-009-9601-1.

The invention claimed is:

1. A method of amplifying an archaea thermosome polynucleotide, if present, from at least one archaea organism comprising:

a) providing a sample comprising at least one archaea thermosome polynucleotide target;

b) adding a primer set for amplifying an archaea thermosome polynucleotide
wherein the primer set comprises:

i) one or more upstream primers comprising a polynucleotide comprising at least 10 contiguous nucleotides of: $GGX_{1u} CCX_{2u} X_{3u} X_{4u} X_{5u} GGX_{6u}$ $X_{7u} TX_{8u} GAX_{9u} AAX_{10u} ATG$ (SEQ ID NO:1); and one or more downstream primers comprising a polynucleotide comprising at least 10 contiguous nucleotides of: $GCX_{1d} AX_{2d}X_{3d} TCX_{4d} TCX_{5d}$ $ATX_{6d} CCX_{7d} TTX_{8d} TG$ (SEQ ID NO:2); or ii) one or more upstream primers comprising a polyucleotide comprising at least 10 contiguous nucleotides of a sequence reverse complementary to: $GGX_{1u} CCX_{2u} X_{3u}X_{4u}X_{5u} GGX_{6u} X_{7u} TX_{8u}$ $GAX_{9u} AAX_{10u} ATG$ (SEQ ID NO:1); and one or more downstream primers comprising a polynucleotide comprising at least 10 contiguous nucleotides of a sequence reverse complementary to: GCX$_{1d}$ AX$_{2d}$ X$_{3d}$ TCX$_{4d}$ TCX$_{5d}$ ATX$_{6d}$ CCX$_{7d}$ TTX$_{8d}$ TG(SEQ ID NO:2)

wherein

X$_{1u}$ is I or C; X$_{2u}$ is I or G; X$_{3u}$ is A or C; X$_{4u}$ is A or G; X$_{5u}$ is A or G; X$_{6u}$ is I or C; X$_{7u}$ is I or A; X$_{8u}$ is I or G; X$_{9u}$ is C or T; X$_{10u}$ is A or G;

X$_{1d}$ is I or C; X$_{2d}$ is I or T; X$_{3d}$ is I or G; X$_{4d}$ is A or G; X$_{5d}$ is I or G; X$_{6d}$ is I or G; X$_{7d}$ is C or T; and X$_{8d}$ is C or T; and wherein the polynucleotide corresponds to a portion of an archaea thermosome polynucleotide;

c) incubating the sample under conditions and with reagents for DNA amplification:

wherein each primer is annealed to the thermosome polynucleotide target at a position enabling amplification of the thermosome polynucleotide target and a DNA polymerase amplifies the thermosome polynucleotide target.

2. The method of claim 1, wherein the thermosome DNA target is thermosom a genomic DNA or thermosome cDNA: optionally, wherein the polynucleotide target has a G+C content of less than about 68%.

3. The method according to claim 1, wherein the primer set comprises an upstream primer comprising a polynucleotide consisting of GGI CCI MRR GGI ITI GAY AAR ATG (SEQ ID NO:3), and a downstream primer comprising a polynucleotide consisting of GCC ATG TCG TCG ATG CCC TTC TG (SEQ ID NO:6).

4. The method according to claim 1, wherein the primer set comprises:

i) a first primer pair comprising a polynucleotide consisting of GGI CCI MRR GGI ITI GAY AAR ATG (SEQ ID NO:3) and a polynucleotide consisting of GCI All TCR TCI ATI CCY TTY TG (SEQ ID NO:4), and a second primer pair comprising a polynucleotide consisting of GGC CCG AAG GGC ATG GAC AAG ATG (SEQ ID NO:5) and a polynucleotide consisting of GCC ATG TCG TCG ATG CCC TTC TG (SEQ ID NO:6), wherein the ratio of the first primer pair to the second primer pair is about 1.1;

ii) a first primer pair comprising a polynucleotide consisting of GGI CCI MRR GGI ITI GAY AAR ATG (SEQ ID NO:3) and a polynucleotide consisting of GCI All TCR TCI ATI CCY TTY TG (SEQ ID NO:4) and a second primer pair comprising a polynucleotide consisting of GGC CCG AAG GGC ATG GAC AAG ATG (SEQ ID NO:5) and a polynucleotide consisting of GCC ATG TCG TCG ATG CCC TTC TG (SEQ ID NO:6), wherein the ratio of the first primer pair to the second primer pair is about 3:1; or iii) a first primer pair comprising a polynucleotide consisting of GGI CCI MRR GGI ITI GAY AAR ATG (SEQ ID NO:3) and a polynucleotide consisting of GCI All TCR TCI ATI CCY TTY TG (SEQ ID NO:4) and a second primer pair comprising a polynucleotide consisting of GGC CCG AAG GGC ATG GAC AAG ATG (SEQ ID NO:5) and a polynucleotide consisting of GCC ATG TCG TCG ATG CCC TTC TG (SEQ ID NO:6) wherein the ratio of the first primer pair ot the second primer pair is about 7:1.

5. The method according to claim 1, wherein the method comprises polvmerase chain reaction (PCR); optionally, wherein the conditions for DNA amplification comprise an annealing temperature from about 45° C to about 58° C; or from about 48° C to about 54° C.

6. A method of detecting the presence or absence of at least one archaea organism in a sample comprising amplifying an archaea thermosome polynucleotide according to the method of claim 1 to provide an amplified thermosome polynucleotide and detecting the amplified thermosome polynucleotide, wherein the detection of the amplified thermosome polynucleotide is indicative of the presence of the archaea organism in the sample.

7. The method according to claim 1, further comprising quantitating the amplified thermosome polynucleotide.

8. A method for identifying a species or nearest phylogenetic neighbor of an archaea organism comprising:
a) amplifying an archaea thermosome polynucleotide according to the method of claim 1 to provide an amplified thermosorne polynucleotide;
b) determining the amplified thermosome polynucleotide sequence;
c) comparing the amplified thermosome polynucleotide sequence to one or more corresponding thermosome nucleotide sequences of known archaea species; and
d) identifying the species or nearest phylogenetic neighbor based on the percent sequence identity between the amplified thermosome polynucleotide sequence and the one or more corresponding thermosome nucleotide sequences of known archaea species.

9. The method according to claim 1, wherein the archaea organism is comprised in a sample selected from a clinical sample rumen contents, intestinal contents, an environmental sample such as a soil sample, a water sample or an anaerobic digester sample.

10. The method according to claim 9, wherein the rumen. contents are obtained from a cow, goat, sheep, bison or deer.

11. The method according to claim 6, wherein the method is for assessing animal nutrition and/or animal health; or for manacling waste from ruminants.

12. A method of detecting the presence or absence of at least one archaea organism in a sample comprising amplifying an archaea thermosome polynucleotide according to the method of claim 3 to provide an amplified thermosome polynucleotide and detecting the amplified thermosome polynucleotide, wherein the detection of the amplified thermosome polynucleotide is indicative of the presence of the archaea organism in the sample.

13. A method of detecting the presence or absence of at least one archaea organism in a sample comprising amplifying an archaea thermosome polynucleotide according to the method of claim 4 to provide an amplified thermosome polynucleotide and detecting the amplified thermosome polynucleotide, wherein the detection of the amplified thermosome polynucleotide is indicative of the presence of the archaea organism in the sample.

14. The method according to claim 6, further comprising quantitating the amplified thermosome polynucleotide.

15. A method for identifying a species or nearest phylogenetic neighbor of an archaea organism comprising:
a) amplifying an archaea thermosome polynucleotide according to the method of claim 3 to provide an amplified thermosome polynucleotide;
b) determining the amplified thermosome polynucleotide sequence;
c) comparing the amplified thermosome polynucleotide sequence to one or more corresponding thermosome nucleotide sequences of known archaea species; and
d) identifying the species or nearest phylogenetic neighbor based on the percent sequence identity between the amplified thermosome polynucleotide sequence and the one or more corresponding thermosome nucleotide sequences of known archaea species.

16. A method for identifying a species or nearest phylogenetic neighbor of an archaea organism comprising:
  a) amplifying an archaea thermosome polynucleotide according to the method of claim 4 to provide an amplified thermosome polynucleotide;
  b) determining the amplified thermosome polynucleotide sequence; and
  c) comparing the amplified thermosome polynucleotide sequence to one or more corresponding thermosome nucleotide sequences of known archaea species; and
  d) identifying the species or nearest phylogenetic neighbor based on the percent sequence identity between the amplified thermosome polynucleotide sequence and the one or more corresponding thermosome nucleotide sequences of known archaea species.

17. The method according to claim 3, wherein the archaea organism is comprised in a sample selected from a clinical sample, rumen contents, intestinal contents, an environmental sample such as a soil sample, a water sample or an anaerobic digestor sample.

18. The method according to claim 4, wherein the archaea organism is comprised in a sample selected from a clinical sample, rumen contents, intestinal contents, an environmental sample such as a soil sample, a water sample or an anaerobic digestor sample.

19. The method according to claim 6, wherein the archaea organism is comprised in a sample selected from a clinical sample, rumen contents, intestinal contents, environmental sample such as a soil sample, a water sample or an anaerobic digestor sample.

20. The method according to claim 7, wherein the archaea organism is comprised in a sample selected from a clinical sample, rumen contents, intestinal contents, an environmental sample such as a soil sample, a water sample or an anaerobic diaestor sample.

21. The method according to claim 8, wherein the archaea organism is comprised in a sample selected from a clinical sample, rumen contents, intestinal contents, an environmental sample such as a soil sample, a water sample or an anaerobic digestor sample.

22. The method according to claim 21, wherein the method is for assessing animal nutrition and/or animal health; or for managing waste from rumninants.

23. The method of claim 1, wherein the at least one archaea thermosome polynucleotide target comprises a G+C content of about 25% to about 70%.

* * * * *

UNITED STATES PATENT AND TRADEMARK OFFICE
CERTIFICATE OF CORRECTION

PATENT NO. : 8,758,999 B2  Page 1 of 1
APPLICATION NO. : 13/637487
DATED : June 24, 2014
INVENTOR(S) : Janet Elizabeth Hill et al.

It is certified that error appears in the above-identified patent and that said Letters Patent is hereby corrected as shown below:

In the Claims

Column 39, line 20, "...target is thermosom a genomic..." should read as --...target is thermosome genomic...--

Column 39, line 58, "...TCG TCG ATG CCC TTC TG (SEQ ID NO:6) wherein..." should read as --...TCG TCG ATG CCC TTC TG (SEQ ID NO:6), wherein...--

Column 39, line 62, "...comprises polvmerase chain reaction..." should read as --...comprises polymerase chain reaction...--

Column 40, line 27, "...sample rumen contents, intestinal..." should read as --...sample, rumen contents, intestinal...--

Column 40, line 30, "...to claim 9, wherein the rumen. contents..." should read as --...to claim 9, wherein the rumen contents...--

Signed and Sealed this
Seventeenth Day of February, 2015

Michelle K. Lee
*Deputy Director of the United States Patent and Trademark Office*